(12) United States Patent
Song et al.

(10) Patent No.: US 11,072,651 B2
(45) Date of Patent: Jul. 27, 2021

(54) ANTIBODY SPECIFICALLY BINDING TO IL-17A, ENCODING NUCLEIC ACID, AND METHOD OF USING THE ANTIBODY

(71) Applicant: Beijing Hanmi Pharm. Co., Ltd., Beijing (CN)

(72) Inventors: Nanmeng Song, Beijing (CN); Jiawang Liu, Beijing (CN); Yaping Yang, Beijing (CN); Yang Yang, Beijing (CN); Dongge Yang, Beijing (CN); Hongjuan Zhang, Beijing (CN); Mengxie Jin, Beijing (CN)

(73) Assignee: BEIJING HANMI PHARM. CO., LTD., Beijing (CN)

( * ) Notice: Subject to any disclaimer, the term of this patent is extended or adjusted under 35 U.S.C. 154(b) by 115 days.

(21) Appl. No.: 16/332,900

(22) PCT Filed: Sep. 8, 2017

(86) PCT No.: PCT/CN2017/101083
§ 371 (c)(1),
(2) Date: Mar. 13, 2019

(87) PCT Pub. No.: WO2018/050028
PCT Pub. Date: Mar. 22, 2018

(65) Prior Publication Data
US 2019/0256588 A1   Aug. 22, 2019

(30) Foreign Application Priority Data
Sep. 14, 2016  (CN) .......................... 201610827097.2

(51) Int. Cl.
| | | |
|---|---|---|
| *A61K 39/395* | (2006.01) | |
| *C07K 16/24* | (2006.01) | |
| *A61K 47/68* | (2017.01) | |
| *A61K 49/00* | (2006.01) | |
| *A61K 49/16* | (2006.01) | |
| *A61K 49/22* | (2006.01) | |
| *A61K 51/10* | (2006.01) | |
| *A61P 19/08* | (2006.01) | |
| *A61P 43/00* | (2006.01) | |
| *A61P 27/02* | (2006.01) | |
| *A61P 11/00* | (2006.01) | |
| *A61P 11/06* | (2006.01) | |
| *A61P 17/06* | (2006.01) | |
| *A61P 37/08* | (2006.01) | |
| *A61P 19/02* | (2006.01) | |
| *A61P 1/12* | (2006.01) | |
| *A61P 17/14* | (2006.01) | |
| *A61P 17/00* | (2006.01) | |
| *A61P 25/00* | (2006.01) | |
| *A61P 31/04* | (2006.01) | |
| *A61P 1/04* | (2006.01) | |
| *A61P 37/06* | (2006.01) | |
| *A61P 7/06* | (2006.01) | |
| *A61P 29/00* | (2006.01) | |

(Continued)

(52) U.S. Cl.
CPC .......... *C07K 16/244* (2013.01); *A61K 39/395* (2013.01); *A61K 47/68* (2017.08); *A61K 47/6845* (2017.08); *A61K 49/0058* (2013.01); *A61K 49/16* (2013.01); *A61K 49/221* (2013.01); *A61K 51/1021* (2013.01); *A61P 1/00* (2018.01); *A61P 1/04* (2018.01); *A61P 1/12* (2018.01); *A61P 7/06* (2018.01); *A61P 9/02* (2018.01); *A61P 11/00* (2018.01); *A61P 11/06* (2018.01); *A61P 13/12* (2018.01); *A61P 17/00* (2018.01); *A61P 17/06* (2018.01); *A61P 17/14* (2018.01); *A61P 19/02* (2018.01); *A61P 19/08* (2018.01); *A61P 25/00* (2018.01); *A61P 27/02* (2018.01); *A61P 29/00* (2018.01); *A61P 31/04* (2018.01); *A61P 37/02* (2018.01); *A61P 37/06* (2018.01); *A61P 37/08* (2018.01); *A61P 43/00* (2018.01); *C07K 16/24* (2013.01); *A61K 2039/505* (2013.01); *C07K 2317/24* (2013.01); *C07K 2317/52* (2013.01); *C07K 2317/565* (2013.01); *C07K 2317/567* (2013.01); *C07K 2317/76* (2013.01); *C07K 2317/92* (2013.01); *C07K 2317/94* (2013.01); *Y02A 50/30* (2018.01)

(58) Field of Classification Search
CPC ..... C07K 16/244; A61K 39/395; A61P 17/06; A61P 19/02
See application file for complete search history.

(56) References Cited

U.S. PATENT DOCUMENTS

| | | |
|---|---|---|
| 8,753,843 B2 | 6/2014 | Presta et al. |
| 8,865,166 B2 | 10/2014 | Cochrane et al. |

(Continued)

FOREIGN PATENT DOCUMENTS

| | | |
|---|---|---|
| CN | 101326195 A | 12/2008 |
| CN | 101501072 A | 8/2009 |

(Continued)

OTHER PUBLICATIONS

International Search Report issued in PCT International Application No. PCT/CN2017/101083, dated Nov. 27, 2017, 14 pages.

(Continued)

*Primary Examiner* — Dong Jiang
(74) *Attorney, Agent, or Firm* — RatnerPrestia

(57) ABSTRACT

An antibody specifically binding to IL-17A or a functional fragment thereof. The antibody or functional fragment thereof includes an IL-17A chimeric antibody and a functional fragment thereof, and an IL-17A humanized antibody and a functional fragment thereof.

17 Claims, 9 Drawing Sheets
Specification includes a Sequence Listing.

(51) Int. Cl.
*A61P 13/12* (2006.01)
*A61P 9/02* (2006.01)
*A61P 37/02* (2006.01)
*A61P 1/00* (2006.01)
*A61K 39/00* (2006.01)

(56) References Cited

U.S. PATENT DOCUMENTS

| | | |
|---|---|---|
| 9,315,557 B2 | 4/2016 | Sillacci Melkko et al. |
| 9,862,765 B2 | 1/2018 | Zhang et al. |
| 9,938,342 B2 | 4/2018 | Di Padova et al. |
| 2007/0218065 A1 | 9/2007 | Jaspers et al. |
| 2008/0269467 A1 | 10/2008 | Allan et al. |
| 2008/0269497 A1 | 10/2008 | Allan et al. |
| 2009/0117126 A1 | 5/2009 | Adams et al. |
| 2009/0175881 A1 | 7/2009 | Presta et al. |
| 2009/0280131 A1 | 11/2009 | Di Padova et al. |
| 2009/0317400 A1 | 12/2009 | Masternak et al. |
| 2010/0080812 A1 | 4/2010 | Auer et al. |
| 2010/0086538 A1 | 4/2010 | Rapecki et al. |
| 2010/0266531 A1 | 10/2010 | Hsieh et al. |
| 2010/0266609 A1 | 10/2010 | Adams et al. |
| 2011/0236390 A1 | 9/2011 | Almagro et al. |
| 2012/0183558 A1 | 7/2012 | Adams et al. |
| 2013/0315911 A1 | 11/2013 | Stevens et al. |
| 2015/0175692 A1 | 6/2015 | Di Padova et al. |
| 2016/0272708 A1 | 9/2016 | Chen |
| 2017/0081401 A1 | 3/2017 | Ulitin et al. |

FOREIGN PATENT DOCUMENTS

| | | |
|---|---|---|
| CN | 101646690 A | 2/2010 |
| CN | 104231080 A | 12/2014 |
| CN | 104684571 A | 6/2015 |
| CN | 105073775 A | 11/2015 |
| WO | 2006054059 A1 | 5/2006 |
| WO | 2010034443 A1 | 4/2010 |
| WO | 2011053763 A2 | 5/2011 |
| WO | 2013177101 A2 | 11/2013 |
| WO | 2014206107 A1 | 12/2014 |
| WO | 2015070697 A1 | 5/2015 |
| WO | 2015137843 A1 | 9/2015 |
| WO | 2016113557 A1 | 7/2016 |

OTHER PUBLICATIONS

Columbian Office Action issued in Columbian Application No. NC2019/0002370, dated May 13, 2020 with partial translation, 6 pages.
Liu et al., "Generation and Characterization of Ixekizumab, a Humanized Monoclonal Antibody that Neutralizes Interleukin-17A", Journal of Inflammation Research, 2016, vol. 9, pp. 39-50.
Karle et al., "Secukinumab, a Novel Anti-IL-17A Antibody, Shows Low Immunogenicity Potential in Human In Vitro Assays Comparable to Other Marketed Biotherapeutics with Low Clinical Immunogenicity", MABS, 2016, vol. 8, No. 3, pp. 536-550.
Chinese Office Action for Chinese Application No. 201710822751.5, dated Mar. 27, 2020 with translation, 11 pages.
Extended European Search Report for European Application No. 17850230.8, dated Mar. 31, 2020 10 pages.
Beringer et al., "IL-17 in Chronic Inflammation: From Discovery to Targeting," Trends in Molecular Medicine, Mar. 2016, vol. 22, No. 3, 230-241.
Chabaud et al., "Human Interleukin-17, A T Cell-Derived Proinflammatory Cytokine Produced by the Rheumatoid Synovium," Arthritis & Rheumatism, vol. 42, No. 5, May 1999, 963-970.
Kellner, "Targeting Interleukin-17 in patients with active rheumatoid arthritis: rationale and clinical potential," Therapeutic Advances in Musculoskeletal Disease, Feb. 5, 2013, 0[0] 1-12.
Leung et al., "Construction and Characterization of a Humanized, Internalizing, B-Cell (CD22)-Specific, Leukemia/Lymphoma Antibody, LL2," Molecular Immunology, vol. 32, No. 17, 1995, 1413-1427.
Lin et al., "Interleukin-17 is Required for T Helper 1 Cell Immunity and Host Resistance to the Intracellular Pathogen Francisella tularensis," Immunity 31, 799-810, Nov. 20, 2009.
Lubberts et al., "Treatment With a Neutralizing Anti-Murine Interleukin-17 Antibody After the Onset of Collagen-Induced Arthritis Reduces Joint Inflammation, Cartilage Destruction, and Bone Erosion," Arthritis & Rheumatism, vol. 50, No. 2, Feb. 2004, 650-659.
Miossec et al., "Targeting IL-17 and TH17 cells in chronic inflammation," Nature Reviews/Drug Discovery, vol. 11, Oct. 2012, 763-776.
Miossec et al., "Interleuki-17 and Type 17 Helper T Cells," The New England Journal of Medicine, Aug. 27, 2009; 361:888-898.
Van Den Berg et al., "Th17 cells and IL-17 A-Focus on 8immunopathogenesis and immunotherapeutics," Seminars in Arthritis and Rheumatism 43 (2013) 158-170.
Chilean Office Action issued in Chilean Application No. 201900659, dated Jul. 13, 2020 with partial translation, 14 pages.
Indian Office Action issied in Indian Patent Application No. 201917013105, dated Jun. 7, 2021 with translation, 6 pages.

SEQUENCE LISTING

```
<160> NUMBER OF SEQ ID NOS: 38

<210> SEQ ID NO 1
<211> LENGTH: 11
<212> TYPE: PRT
<213> ORGANISM: Artificial
<220> FEATURE:
<223> OTHER INFORMATION: CDR-L1

<400> SEQUENCE: 1

Gln Ser Leu Val His Ser Asn Gly Asn Thr Tyr
1               5                   10

<210> SEQ ID NO 2
<211> LENGTH: 7
<212> TYPE: PRT
<213> ORGANISM: Artificial
<220> FEATURE:
<223> OTHER INFORMATION: CDR-L2

<400> SEQUENCE: 2

Lys Val Tyr Asn Arg Phe Ser
1               5

<210> SEQ ID NO 3
<211> LENGTH: 7
<212> TYPE: PRT
<213> ORGANISM: Artificial
<220> FEATURE:
<223> OTHER INFORMATION: CDR-L3

<400> SEQUENCE: 3

Gln Ser Thr His Phe Pro Thr
1               5

<210> SEQ ID NO 4
<211> LENGTH: 8
<212> TYPE: PRT
<213> ORGANISM: Artificial
```

```
<220> FEATURE:
<223> OTHER INFORMATION: CDR-H1

<400> SEQUENCE: 4

Asn Ser Ile Thr Ser Tyr Tyr Ala
1               5

<210> SEQ ID NO 5
<211> LENGTH: 7
<212> TYPE: PRT
<213> ORGANISM: Artificial
<220> FEATURE:
<223> OTHER INFORMATION: CDR-H2

<400> SEQUENCE: 5

Thr Tyr Ser Gly Thr Thr Ser
1               5

<210> SEQ ID NO 6
<211> LENGTH: 13
<212> TYPE: PRT
<213> ORGANISM: Artificial
<220> FEATURE:
<223> OTHER INFORMATION: CDR-H3

<400> SEQUENCE: 6

Ala Arg Glu Glu Tyr Asp Asp Ile Tyr Ala Val Asp Tyr
1               5                   10

<210> SEQ ID NO 7
<211> LENGTH: 111
<212> TYPE: PRT
<213> ORGANISM: Artificial
<220> FEATURE:
<223> OTHER INFORMATION: Light chain variable region

<400> SEQUENCE: 7

Ile Ile Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Thr Phe Gly Gly Gly Thr Lys Leu Glu Ile Lys
            100                 105                 110

<210> SEQ ID NO 8
<211> LENGTH: 120
<212> TYPE: PRT
<213> ORGANISM: Artificial
<220> FEATURE:
<223> OTHER INFORMATION: Heavy chain variable region

<400> SEQUENCE: 8

Asp Val Gln Val Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Tyr
```

```
                    20                  25                  30

Tyr Ala Trp Asn Trp Ile Arg Gln Phe Pro Gly Asn Lys Leu Glu Trp
            35                  40                  45

Met Gly Tyr Ile Thr Tyr Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Glu Glu Tyr Asp Asp Ile Tyr Ala Val Asp Tyr Trp Gly Gln
            100                 105                 110

Gly Thr Ser Val Thr Val Ser Ser
            115                 120

<210> SEQ ID NO 9
<211> LENGTH: 107
<212> TYPE: PRT
<213> ORGANISM: Artificial
<220> FEATURE:
<223> OTHER INFORMATION: Light chain constant region

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 330
<212> TYPE: PRT
<213> ORGANISM: Artificial
<220> FEATURE:
<223> OTHER INFORMATION: Heavy chain constant region

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 26
<212> TYPE: PRT
<213> ORGANISM: Artificial
<220> FEATURE:
<223> OTHER INFORMATION: Light chain framework region FR-L1

<400> SEQUENCE: 11

Asp Val Val Met Thr Gln Ser Pro Leu Ser Leu Pro Val Thr Leu Gly
1               5                   10                  15

Gln Pro Ala Ser Ile Ser Cys Arg Ser Ser
            20                  25

<210> SEQ ID NO 12
<211> LENGTH: 17
<212> TYPE: PRT
<213> ORGANISM: Artificial
<220> FEATURE:
<223> OTHER INFORMATION: Light chain framework region FR-L2

<400> SEQUENCE: 12

Leu His Trp Phe Gln Gln Arg Pro Gly Gln Ser Pro Arg Arg Leu Ile
1               5                   10                  15

Tyr

<210> SEQ ID NO 13
<211> LENGTH: 36
```

```
<212> TYPE: PRT
<213> ORGANISM: Artificial
<220> FEATURE:
<223> OTHER INFORMATION: Light chain framework region FR-L3

<400> SEQUENCE: 13

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 14
<211> LENGTH: 10
<212> TYPE: PRT
<213> ORGANISM: Artificial
<220> FEATURE:
<223> OTHER INFORMATION: Light chain framework region FR-L4

<400> SEQUENCE: 14

Phe Gly Gln Gly Thr Arg Leu Glu Ile Lys
1               5                   10

<210> SEQ ID NO 15
<211> LENGTH: 25
<212> TYPE: PRT
<213> ORGANISM: Artificial
<220> FEATURE:
<223> OTHER INFORMATION: Heavy chain framework region FR-H1

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 16
<211> LENGTH: 17
<212> TYPE: PRT
<213> ORGANISM: Artificial
<220> FEATURE:
<223> OTHER INFORMATION: Heavy chain framework region FR-H2

<400> SEQUENCE: 16

Trp Asn Trp Ile Arg Gln Pro Pro Gly Lys Gly Leu Glu Trp Ile Gly
1               5                   10                  15

Tyr

<210> SEQ ID NO 17
<211> LENGTH: 30
<212> TYPE: PRT
<213> ORGANISM: Artificial
<220> FEATURE:
<223> OTHER INFORMATION: Heavy chain framework region FR-H3

<400> SEQUENCE: 17

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 18
<211> LENGTH: 11
```

```
<212> TYPE: PRT
<213> ORGANISM: Artificial
<220> FEATURE:
<223> OTHER INFORMATION: Heavy chain framework region FR-H4

<400> SEQUENCE: 18

Trp Gly Gln Gly Thr Leu Val Thr Val Ser Ser
1               5                   10

<210> SEQ ID NO 19
<211> LENGTH: 111
<212> TYPE: PRT
<213> ORGANISM: Artificial
<220> FEATURE:
<223> OTHER INFORMATION: Light chain variable region

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Thr Phe Gly Gln Gly Thr Arg Leu Glu Ile Lys
            100                 105                 110

<210> SEQ ID NO 20
<211> LENGTH: 111
<212> TYPE: PRT
<213> ORGANISM: Artificial
<220> FEATURE:
<223> OTHER INFORMATION: Light chain variable region

<400> SEQUENCE: 20

Ile Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Thr Phe Gly Gly Gly Thr Lys Leu Glu Ile Lys
            100                 105                 110

<210> SEQ ID NO 21
<211> LENGTH: 111
<212> TYPE: PRT
<213> ORGANISM: Artificial
<220> FEATURE:
<223> OTHER INFORMATION: Light chain variable region
```

<400> SEQUENCE: 21

Ile Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Arg Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Thr Phe Gly Gln Gly Thr Arg Leu Glu Ile Lys
            100                 105                 110

<210> SEQ ID NO 22
<211> LENGTH: 111
<212> TYPE: PRT
<213> ORGANISM: Artificial
<220> FEATURE:
<223> OTHER INFORMATION: Light chain variable region

<400> SEQUENCE: 22

Ile Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro Thr Phe Gly Gln Gly Thr Arg Leu Glu Ile Lys
            100                 105                 110

<210> SEQ ID NO 23
<211> LENGTH: 111
<212> TYPE: PRT
<213> ORGANISM: Artificial
<220> FEATURE:
<223> OTHER INFORMATION: Light chain variable region

<400> SEQUENCE: 23

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Arg Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Thr Phe Gly Gln Gly Thr Arg Leu Glu Ile Lys
            100                 105                 110

<210> SEQ ID NO 24
<211> LENGTH: 111
<212> TYPE: PRT
<213> ORGANISM: Artificial
<220> FEATURE:
<223> OTHER INFORMATION: Light chain variable region

<400> SEQUENCE: 24

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Thr Phe Gly Gln Gly Thr Arg Leu Glu Ile Lys
            100                 105                 110

<210> SEQ ID NO 25
<211> LENGTH: 111
<212> TYPE: PRT
<213> ORGANISM: Artificial
<220> FEATURE:
<223> OTHER INFORMATION: Light chain variable region

<400> SEQUENCE: 25

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Leu Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Thr Phe Gly Gln Gly Thr Arg Leu Glu Ile Lys
            100                 105                 110

<210> SEQ ID NO 26
<211> LENGTH: 111
<212> TYPE: PRT
<213> ORGANISM: Artificial
<220> FEATURE:
<223> OTHER INFORMATION: Light chain variable region

<400> SEQUENCE: 26

-continued

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro Thr Phe Gly Gln Gly Thr Arg Leu Glu Ile Lys
            100                 105                 110

<210> SEQ ID NO 27
<211> LENGTH: 120
<212> TYPE: PRT
<213> ORGANISM: Artificial
<220> FEATURE:
<223> OTHER INFORMATION: Heavy chain variable region

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Asn Ser Ile Thr Ser Tyr
            20                  25                  30

Tyr Ala Trp Asn Trp Ile Arg Gln Pro Pro Gly Lys Gly Leu Glu Trp
        35                  40                  45

Ile Gly Tyr Ile Thr Tyr Ser Gly Thr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
            100                 105                 110

Gly Thr Leu Val Thr Val Ser Ser
        115                 120

<210> SEQ ID NO 28
<211> LENGTH: 120
<212> TYPE: PRT
<213> ORGANISM: Artificial
<220> FEATURE:
<223> OTHER INFORMATION: Heavy chain variable region

<400> SEQUENCE: 28

Asp Val Gln Val Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Tyr
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Glu Asp Thr Ala Thr Tyr Tyr Cys
                85                  90                  95

Ala Arg Glu Glu Tyr Asp Asp Ile Tyr Ala Val Asp Tyr Trp Gly Gln
            100                 105                 110

Gly Thr Ser Val Thr Val Ser Ser
            115                 120

<210> SEQ ID NO 29
<211> LENGTH: 120
<212> TYPE: PRT
<213> ORGANISM: Artificial
<220> FEATURE:
<223> OTHER INFORMATION: Heavy chain variable region

<400> SEQUENCE: 29

Gln Val Gln Val Gln Glu Ser Gly Pro Gly Leu Val Lys Pro Ser Glu
1               5                   10                  15

Thr Leu Ser Leu Thr Cys Thr Val Ser Gly Asn Ser Ile Thr Ser Tyr
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Thr Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
            100                 105                 110

Gly Thr Leu Val Thr Val Ser Ser
            115                 120

<210> SEQ ID NO 30
<211> LENGTH: 120
<212> TYPE: PRT
<213> ORGANISM: Artificial
<220> FEATURE:
<223> OTHER INFORMATION: Heavy chain variable region

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Thr Val Ser Gly Asn Ser Ile Thr Ser Tyr
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Thr Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
            100                 105                 110

Gly Thr Leu Val Thr Val Ser Ser
            115                 120

```
<210> SEQ ID NO 31
<211> LENGTH: 120
<212> TYPE: PRT
<213> ORGANISM: Artificial
<220> FEATURE:
<223> OTHER INFORMATION: Heavy chain variable region

<400> SEQUENCE: 31

Gln Val Gln Val Gln Glu Ser Gly Pro Gly Leu Val Lys Pro Ser Glu
1               5                   10                  15

Thr Leu Ser Leu Thr Cys Thr Val Ser Gly Asn Ser Ile Thr Ser Tyr
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Thr Thr Ser Tyr Asn Pro Ser Leu
    50                  55                  60

Lys Ser Arg Ile Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
            100                 105                 110

Gly Thr Leu Val Thr Val Ser Ser
        115                 120

<210> SEQ ID NO 32
<211> LENGTH: 120
<212> TYPE: PRT
<213> ORGANISM: Artificial
<220> FEATURE:
<223> OTHER INFORMATION: Heavy chain variable region

<400> SEQUENCE: 32

Gln Val Gln Val Gln Glu Ser Gly Pro Gly Leu Val Lys Pro Ser Glu
1               5                   10                  15

Thr Leu Ser Leu Thr Cys Thr Val Ser Gly Asn Ser Ile Thr Ser Tyr
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Thr Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
            100                 105                 110

Gly Thr Leu Val Thr Val Ser Ser
        115                 120

<210> SEQ ID NO 33
<211> LENGTH: 120
<212> TYPE: PRT
<213> ORGANISM: Artificial
<220> FEATURE:
<223> OTHER INFORMATION: Heavy chain variable region

<400> SEQUENCE: 33

Gln Val Gln Val Gln Glu Ser Gly Pro Gly Leu Val Lys Pro Ser Glu
1               5                   10                  15
```

Thr Leu Ser Leu Thr Cys Thr Val Ser Gly Asn Ser Ile Thr Ser Tyr
            20                  25                  30

Tyr Ala Trp Asn Trp Ile Arg Gln Pro Pro Gly Lys Gly Leu Glu Trp
                35                  40                  45

Met Gly Tyr Ile Thr Tyr Ser Gly Thr Thr Ser Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
            100                 105                 110

Gly Thr Leu Val Thr Val Ser Ser
            115                 120

<210> SEQ ID NO 34
<211> LENGTH: 120
<212> TYPE: PRT
<213> ORGANISM: Artificial
<220> FEATURE:
<223> OTHER INFORMATION: Heavy chain variable region

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Thr Val Ser Gly Asn Ser Ile Thr Ser Tyr
            20                  25                  30

Tyr Ala Trp Asn Trp Ile Arg Gln Pro Pro Gly Lys Gly Leu Glu Trp
                35                  40                  45

Met Gly Tyr Ile Thr Tyr Ser Gly Thr Thr Ser Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
            100                 105                 110

Gly Thr Leu Val Thr Val Ser Ser
            115                 120

<210> SEQ ID NO 35
<211> LENGTH: 98
<212> TYPE: PRT
<213> ORGANISM: Artificial
<220> FEATURE:
<223> OTHER INFORMATION: IGVH4-59*01 (Germline database)
<220> FEATURE:
<221> NAME/KEY: MISC_FEATURE
<222> LOCATION: (98)..(98)
<223> OTHER INFORMATION: Xaa can be any naturally occurring amino acid

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
                35                  40                  45

```
Gly Tyr Ile Tyr Tyr Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Xaa

<210> SEQ ID NO 36
<211> LENGTH: 101
<212> TYPE: PRT
<213> ORGANISM: Artificial
<220> FEATURE:
<223> OTHER INFORMATION: IGKV2-30*02 (Germline database)

<400> SEQUENCE: 36

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val His Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro
            100

<210> SEQ ID NO 37
<211> LENGTH: 120
<212> TYPE: PRT
<213> ORGANISM: Artificial
<220> FEATURE:
<223> OTHER INFORMATION: Grafted humanized antibody heavy chain variable
      region

<400> SEQUENCE: 37

Gln Val Gln Leu Gln Glu Ser Gly Pro Gly Leu Val Lys Pro Ser Glu
  1               5                  10                  15

Thr Leu Ser Leu Thr Cys Thr Val Ser Gly Asn Ser Ile Thr Ser Tyr
                 20                  25                  30

Tyr Ala Trp Asn Trp Ile Arg Gln Pro Pro Gly Lys Gly Leu Glu Trp
             35                  40                  45

Ile Gly Tyr Ile Thr Tyr Ser Gly Thr Thr Ser Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Glu Tyr Asp Asp Ile Tyr Ala Val Asp Tyr Trp Gly Gln
                100                 105                 110

Gly Thr Leu Val Thr Val Ser Ser
            115                 120

<210> SEQ ID NO 38
```

```
<211> LENGTH: 111
<212> TYPE: PRT
<213> ORGANISM: Artificial
<220> FEATURE:
<223> OTHER INFORMATION: Grafted humanized antibody light chain variable
      region

<400> SEQUENCE: 38

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Thr Phe Gly Gln Gly Thr Arg Leu Glu Ile Lys
                100                 105                 110
```

ANTIBODY SPECIFICALLY BINDING TO IL-17A, ENCODING NUCLEIC ACID, AND METHOD OF USING THE ANTIBODY

This application is the U.S. National Phase Application of PCT/CN2017/101083, filed Sep. 8, 2017, which claims priority to Chinese Patent Application No. CN201610827097.2, filed on Sep. 14, 2016 with State Intellectual Property Office and entitled "ANTIBODY SPECIFICALLY BINDING TO IL-17A AND FUNCTIONAL FRAGMENT THEREOF", the contents of such applications being incorporated by reference herein.

The present disclosure relates to the field of medical biotechnology and humanized antibody engineering research, and in particular to an antibody specifically binding to IL-17A and functional fragments thereof.

BACKGROUND

Interleukin-17A (IL-17 or IL-17A) is a pro-inflammatory cytokine produced primarily by Th17 cells and is the most representative member of the IL-17 family (Miossec P, Kolls J K. Nat. Rev. Drug. Discov., 2012, 11: 763-776). After binding to IL-17A receptor (IL-17RA), IL-17A may induce the expression of inflammatory cytokines and chemokines in a variety of cells (such as fibroblasts, epithelial cells, and endothelial cells), playing an important role in body immunological defense (Lin Y, Ritchea S, Logar A. Immunity, 2009, 31:799-810).

However, over-expressed IL-17A may cause many inflammatory diseases. For example, IL-17A has effects on macrophages and DC cells, inducing high expression of IL-1, IL-6, TNF and CRP, resulting in inflammatory reaction, and involving in the pathological processes of psoriasis and transplant rejection. IL-17A has effects on endothelial cells, inducing high expression of IL-6, MMP and coagulation factors, resulting in vascular activation, and involving in pathological processes of reperfusion injury, thrombosis and atherosclerosis. IL-17A has effects on fibroblasts, inducing high expression of IL-6, chemokines, growth factors and MMP, resulting in matrix destruction, and involving in the pathological process of multiple sclerosis and Crohn's disease. IL-17A has effects on osteoblasts and chondrocytes, inducing RANKL, MMP and osteoclast genesis, resulting in bone erosion and cartilage damage, and involving in the pathological process of rheumatoid arthritis and periodontal disease (N Engl J Med. 2009 Aug. 27; 361(9):888-98. Nat Rev Drug Discov. 2012 October; 11(10):763-76. Semin Arthritis Rheum. 2013 October; 43(2):158-70. Trends Mol Med. 2016 March; 22(3):230-41).

IL-17A neutralizing antibody can inhibit the high expression of IL-17A in synovial tissue of patients with rheumatoid arthritis and reduce the production of important inflammatory factor IL-6 (Chabaud M, Durand J M, Buchs N, et al. Arthritis Rheum. 1999, 42: 963-70). It has been demonstrated by many animal model experiments of autoimmune diseases that the use of antibodies to neutralize IL-17A can effectively inhibit the pathological development of inflammation (Lubberts E, Koenders M I, Oppers-Walgreen B, et al. Arthritis Rheum., 2004, 50: 650-659).

Currently, IL-17A-related antibody drugs, Secukinumab (IL-17A targeting antibody) and Ixekizumab (IL-17A targeting antibody), have been approved for marketing, which are both used for the treatment of psoriasis. However, results of drug clinical trial have shown that these drugs do not show the expected therapeutic effect for certain chronic inflammatory diseases such as rheumatoid arthritis (Kellner H, Ther Adv Musculoskelet Dis., 2013, 5: 141-152).

In view of this, the present disclosure has been specifically proposed.

SUMMARY

The present disclosure is based on an obtained parental anti-human IL-17A murine monoclonal antibody having the ability to specifically bind to human IL-17A protein, by cloning, identification and gene structure analysis to determine its CDR region, construct corresponding chimeric antibody and humanized antibody, establish corresponding eukaryotic cell expression system and produce and purify the chimeric antibody and the humanized antibody.

In order to achieve the above-mentioned goal of the present disclosure, the following technical solutions are specially adopted:

An antibody capable of specifically binding to IL-17A and a functional fragment thereof, wherein the antibody or the functional fragment thereof comprise a light chain and a heavy chain;

the light chain comprises a light chain CDR consisting of CDR-L1, CDR-L2 and CDR-L3; the heavy chain comprises a heavy chain CDR consisting of CDR-H1, CDR-H2 and CDR-H3;

the amino acid sequences of the CDR-L1, CDR-L2 and CDR-L3 are respectively set forth in SEQ ID NO: 1, 2 and 3; the amino acid sequences of the CDR-H1, CDR-H2 and CDR-H3 are respectively set forth in SEQ ID NO: 4, 5 and 6.

Preferably, the antibody or the functional fragment thereof includes an IL-17A chimeric antibody and a functional fragment thereof, and an IL-17A humanized antibody and a functional fragment thereof.

Preferably, the antibody or the functional fragment thereof includes an IL-17A chimeric antibody and a functional fragment thereof, and an IL-17A humanized antibody and a functional fragment thereof.

That is, the antibody or the functional fragment thereof includes an IL-17A chimeric antibody and a functional fragment thereof, or the antibody or the functional fragment thereof includes an IL-17A humanized antibody and a functional fragment thereof.

It is well known in the art that both the binding specificity and affinity of an antibody are mainly determined by the CDR, and the amino acid sequence of the non-CDR region can be easily changed according to the well-known existing techniques to obtain a variant having similar biological activities. In the present disclosure, the monoclonal antibody variants have CDR sequences identical to the CDR sequences of above-mentioned humanized antibodies, thus, they have similar biological activities.

Preferably, the antibody and the functional fragment thereof as described above, wherein the antibody comprises a constant region sequence of any one selected from the group consisting of human IgG1, IgG2, IgG3, IgG4, IgA, IgM, IgE and IgD.

Preferably, the antibody and the functional fragment thereof as described above, wherein the functional fragment comprises one or more selected from the group consisting of $F(ab')_2$, Fab', Fab, Fv, scFv, bispecific antibody and antibody minimal recognition unit.

The "functional fragment" of the present disclosure specifically refers to an antibody fragment having the same specificity to IL-17A as that of the parent antibody. In addition to the above mentioned functional fragments, any fragment of which half-life has been increased may be also included.

scFv (sc=single strand), bispecific antibody (diabodies).

These functional fragments typically have the same binding specificity as the antibody from which they are derived. One ordinary skill in the art can learn from what is described in the specification of the present disclosure that the antibody fragment of the present disclosure and obtain the above mentioned function fragment by a method such as enzymatic digestion (including pepsin or papain) and/or a method of chemically reducing split disulfide bonds.

The antibody fragments can also be obtained by peptide synthesis by recombinant genetic techniques, which are also known to those having ordinary skill in the art, or by automated peptide synthesizers such as an automated peptide synthesizer sold by such as Applied BioSystems.

Preferably, the antibody and the functional fragment thereof as described above, wherein the amino acid sequences of light chain variable region and heavy chain variable region of the IL-17A chimeric antibody and the functional fragment thereof are respectively set forth in SEQ ID NO: 7 and SEQ ID NO:8;

Further preferably, the antibody and the functional fragment thereof as described above, wherein the amino acid sequence of the light chain constant region and the heavy chain constant region of the IL-17A chimeric antibody and functional fragment thereof are respectively set forth in SEQ ID NO: 9 and SEQ ID NO: 10.

Preferably, the antibody and the functional fragment thereof as described above, wherein light chain framework region of the IL-17A humanized antibody and the functional fragment thereof comprises FR-L1, FR-L2, FR-L3 and FR-L4, and heavy chain framework region of the IL-17A humanized antibody and the functional fragment thereof comprises FR-H1, FR-H2, FR-H3 and FR-H4.

The amino acid sequences of FR-L1, FR-L2, FR-L3 and FR-L4 are set forth in SEQ ID NO: 11 to 14 respectively.

The amino acid sequences of the FR-H1, FR-H2, FR-H3 and FR-H4 are set forth in SEQ ID NO: 15 to 18 respectively.

Usually, when transplanting CDRs of a murine antibody to a human framework, selection of a human framework with high sequence homology will have a certain success rate. However, studies have shown that many CDR grafts require a back mutation to restore certain antibody activity. How to choose the right human source framework is the major bottleneck.

The CDR is the major relevant site for antigen binding, but in most cases, the FR (framework region) has a significant influence on the conformation of the binding site. In order to obtain a high affinity humanized antibody, in the present disclosure, a suitable FR region is selected and the relevant FR residue is reversed back to the original murine amino acid or a amino acid presented in human and having the same function.

Preferably, the FR-L1 is selected from the amino acid sequence set forth in SEQ ID NO: 11 and the amino sequence having the following substitution or a combination thereof:

the $1^{st}$ amino acid D is replaced by I;
the $2^{nd}$ amino acid V is replaced by I;
the FR-L2 is selected from the amino acid sequence set forth in SEQ ID NO: 12 and the amino sequence having the following substitution or a combination thereof:
the $4^{th}$ amino acid F is replaced by Y;
the $14^{th}$ amino acid R is replaced by L;

the FR-L3 is selected from the amino acid sequence set forth in SEQ ID NO: 13 and the amino sequence having the following substitution or a combination thereof:
the $35^{th}$ amino acid Y is replaced by F;
the FR-L4 is selected from the amino acid sequence set forth in SEQ ID NO: 14;
the FR-H1 is selected from the amino acid sequence set forth in SEQ ID NO: 15 and the amino sequence having the following substitution or a combination thereof:
the $4^{th}$ amino acid L is replaced by V;
the FR-H2 is selected from the amino acid sequence set forth in SEQ ID NO: 16 and the amino sequence having the following substitution or a combination thereof:
the $15^{th}$ amino acid I is replaced by M;
the FR-H3 is selected from the amino acid sequence set forth in SEQ ID NO: 17 and the amino sequence having the following substitution or a combination thereof:
the $2^{nd}$ amino acid V is replaced by I;
the $6^{th}$ amino acid V is replaced by R;
the FR-H4 is selected from the amino acid sequence set forth in SEQ ID NO: 18;
preferably, light chain variable region sequence of the IL-17A humanized antibody and the functional fragment thereof is one selected from SEQ ID NO: 19-26;
preferably, heavy chain variable region sequence of the IL-17A humanized antibody and the functional fragment thereof is one selected from SEQ ID NO: 27-34;
more preferably, the light chain variable region sequence of the IL-17A humanized antibody and the functional fragment thereof is set forth in SEQ ID NO: 19; the corresponding heavy chain variable region sequence is set forth in SEQ ID NO: 27;
alternatively, the light chain variable region sequence of the IL-17A humanized antibody and the functional fragment thereof is set forth in SEQ ID NO: 20; the corresponding heavy chain variable region sequence is set forth in SEQ ID NO: 28;
alternatively, the light chain variable region sequence of the IL-17A humanized antibody and the functional fragment thereof is set forth in SEQ ID NO: 21; the corresponding heavy chain variable region sequence is set forth in SEQ ID NO: 29;
alternatively, the light chain variable region sequence of the IL-17A humanized antibody and the functional fragment thereof is set forth in SEQ ID NO: 22; the corresponding heavy chain variable region sequence is set forth in SEQ ID NO: 30;
alternatively, the light chain variable region sequence of the IL-17A humanized antibody and the functional fragment thereof is set forth in SEQ ID NO: 22; the corresponding heavy chain variable region sequence is set forth in SEQ ID NO: 31;
alternatively, the light chain variable region sequence of the IL-17A humanized antibody and the functional fragment thereof is set forth in SEQ ID NO: 23; the corresponding heavy chain variable region sequence is set forth in SEQ ID NO: 32;
alternatively, the light chain variable region sequence of the IL-17A humanized antibody and the functional fragment thereof is set forth in SEQ ID NO: 24; the corresponding heavy chain variable region sequence is set forth in SEQ ID NO: 33;
alternatively, the light chain variable region sequence of the IL-17A humanized antibody and the functional fragment thereof is set forth in SEQ ID NO: 25; the corresponding heavy chain variable region sequence is set forth in SEQ ID NO: 32;

alternatively, the light chain variable region sequence of the IL-17A humanized antibody and the functional fragment thereof is set forth in SEQ ID NO: 26; the corresponding heavy chain variable region sequence is set forth in SEQ ID NO: 34;

more preferably, the amino acid sequences of the light chain constant region and the heavy chain constant region of the IL-17A humanized antibody and the functional fragment thereof are respectively set forth in SEQ ID NO: 9 and SEQ ID NO: 10.

The light chain constant region of the IL-17A humanized antibody and the functional fragment thereof is selected from the light chain constant region of human Kappa antibody, of which the amino acid sequence is set forth in SEQ ID NO: 9.

The heavy chain constant region of the IL-17A humanized antibody and the functional fragment thereof is selected from the heavy chain constant region of human IgG1 antibody, of which the amino acid sequence is set forth in SEQ ID NO: 10.

It should be noted that, in addition to the above-mentioned amino acid sequences in the present application, the production of chimeric antibodies and humanized antibodies can be achieved by any method known by those having ordinary skill in the art, such as by designing recombinant humanized antibody based on sequenced CDRs of murine antibodies, the murine antibody is secreted by myeloma cells from immunized mice or by myeloma cells fused to splenocytes of other species which fused to myeloma cells. The immunized animal may include a transgenic mouse having a human immunoglobulin locus which can directly produce a human antibody. Another possible embodiment may include screening the library using phage display technology.

An isolated nucleic acid molecule selected from:

A) DNA or RNA, encoding the antibody and the functional fragment thereof as described above; and B) a nucleic acid complementary to the nucleic acid as defined in A).

A vector, which contains a nucleic acid molecule as described above.

The present disclosure further provides at least one nuclear construct encoding a nucleic acid molecule as described above, preferably a vector, more preferably an expression vector, such as a plasmid, which is described in one embodiment of the present application.

A host cell, which is transformed with a vector as described above.

The host cell is a eukaryotic cell, such as a mammalian cell.

A method of producing an antibody capable of specifically binding to IL-17A and a functional fragment thereof includes the following steps:

culturing host cells as described above in a medium and under suitable culture conditions; and recovering produced antibody and its functional fragments from the culture medium or from the cultured host cells.

A composition, comprising the antibody and/or the functional fragment thereof, or a compound of the antibody and/or the functional fragment thereof together with other components, as an active ingredient.

Preferably, the composition as described above, the antibody and the functional fragment thereof are coupled to at least one diagnostic agent and/or therapeutic agent to form an immunoconjugate.

Preferably, the diagnostic agent is one or more selected from the group consisting of a radionuclide, a radioactive contrast agent, a paramagnetic ion, a metal, a fluorescent label, a chemiluminescent label, an ultrasound contrast agent, and a photosensitizer.

Preferably, the radionuclide is one or more selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb and $^{83}$Sr.

Preferably, the paramagnetic ion is one or more selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

Preferably, the fluorescent label is one or more selected from the group consisting of Alexa 350, Alexa 405, Alexa 430, Alexa 488, Alexa 555, Alexa 647, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxyfluorescein, 5-carboxy-2',4',5',7'-tetrachlorofluorescein, 5-carboxyfluorescein, 5-carboxyrhodamine, 6-carboxyrhodamine, 6-carboxytetramethylrhodamine, Cascade Blue, Cy2, Cy3, Cy5, Cy7, 6-FAM, dansyl chloride, fluorescein, HEX, 6-JOE, NBD (7-nitrobenzo-2-oxa-1,3-diazole), Oregon Green 488, Oregon Green 500, Oregon Green 514, Pacific Blue, phthalic acid, terephthalic acid, isophthalic acid, cresol fast purple, cresyl violet, brilliant cresyl blue, 4-Aminobenzoic acid, erythrosine, phthalocyanine, azomethine, cyanine, xanthine, succinyl fluorescein, rare earth metal cryptate, tri-bipyridyldiamine oxime, europium cryptate compound or chelate, diamine, dicyanine, La Jolla blue dye, allophycocyanin, allococyanin B, phycocyanin C, phycocyanin R, thiamine, R-phycoerythrin, C-Phycocyanin, phycoerythrin R, REG, rhodamine green, rhodamine isothiocyanate, rhodamine red, ROX, TAMRA, TET, TRIT (tetramethylrhodamine isothiol), tetramethylrhodamine and Texas Red.

Preferably, the therapeutic agent is one or more selected from the group consisting of a naked antibody, a cytotoxic agent, a drug, a radionuclide, a boron atom, an immunomodulator, an anti-apoptotic agent, a photosensitizing therapeutic, an immunoconjugates and a oligonucleotide.

Preferably, the drug is one or more selected from the group consisting of methotrexate, fluorouracil, mercaptopurine, hydroxyurea, cytarabine, nitrogen mustard, cyclophosphamide, thiotepa, cisplatin, mitomycin, bleomycin, camptothecin, podophyllotoxin, actinomycin D, doxorubicin, daunorubicin, vinblastine, paclitaxel, cephalotaxus alkaloids and L-asparaginase.

Preferably, the oligonucleotide is one or more selected from the group consisting of shRNA, miRNA and siRNA.

Preferably, the immunomodulator is one or more selected from the group consisting of a cytokine, a chemokine, a stem cell growth factor, a lymphotoxin, a hematopoietic factor, a colony stimulating factor (CSF), an interferon, an erythropoietin, a thrombopoietin, an interleukin (IL), granulocyte-colony stimulating factor (G-CSF), granulocyte macrophage-colony stimulating factor (GM-CSF) and stem cell growth factor.

Wherein, the cytokine is preferably one or more selected from the group consisting of human growth hormone, N-methionyl human growth hormone, bovine growth hormone, parathyroid hormone, thyroxine, insulin, proinsulin, relaxin, prorelaxin, follicle-stimulating hormone (FSH), thyroid stimulating hormone (TSH), luteinizing hormone (LH), liver growth factor, prostaglandin, fibroblast growth factor, prolactin, placental lactogen, OB protein, tumor necrosis factor-α, tumor necrosis factor-β, Mullerian inhibitor, mouse gonadotropin-related peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factor, interferon-α, interferon-β, interferon-γ, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and LT.

The chemokine is preferably one or more selected from the group consisting of RANTES, MCAF, MIP1-α, MIP1-β, and IP-10.

Preferably, the radionuclide is one or more selected from the group consisting of $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$Y, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{86}$Re, $^{188}$Re, $^{189}$Re, $^{211}$Pb, $^{212}$Pb, $^{223}$Ra, $^{225}$Ac, $^{77}$As, $^{89}$Sr, $^{99}$Mo, $^{105}$Rh, $^{149}$Pm, $^{169}$Er, $^{194}$Ir, $^{58}$Co, $^{80m}$Br, $^{99}$mTc, $^{103m}$Rh, $^{109}$Pt, $^{119}$Sb, $^{189m}$Os, $^{192}$Ir, $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br and $^{169}$Yb.

Use of the composition as described above for the manufacture of a medicament in prevention and/or treatment of a disease associated with overexpression and/or over-release of IL-17A.

Preferably, the disease is one or more selected from the group consisting of airway inflammation, asthma, bronchial asthma, allergic asthma, chronic obstructive pulmonary disease, idiopathic pulmonary fibrosis, rheumatoid arthritis, osteoarthritis, ankylosing spondylitis, psoriatic arthritis, psoriasis, multiple sclerosis, systemic sclerosis, systemic lupus erythematosus, lupus nephritis, scleroderma, ulcerative colitis, inflammatory bowel disease, uveitis, *Helicobacter pylori*-associated gastritis, osteoporosis, bone erosion, intraperitoneal abscess and adhesions, Addison's disease, gamma globulin deficiency, alopecia areata, celiac disease, Chagas disease, Crohn's disease, allograft rejection, Behcet's disease, sepsis, septic or endotoxin shock and ischemia.

Use of the antibody capable of specifically binding to IL-17A and the functional fragment thereof as described above for the manufacture of a medicament in prevention and/or treatment of a disease associated with overexpression and/or over-release of IL-17A.

A drug for prevention and/or treatment of a disease associated with overexpression and/or over-release of IL-17A, comprising the antibody capable of specifically binding to IL-17A and the functional fragment thereof, and a pharmaceutically acceptable carrier.

Alternatively, the drug comprises the composition as described above and a pharmaceutically acceptable carrier.

Herein, the term "pharmaceutically acceptable" means that the compound is physiologically acceptable when the compound is administered to a human, and does not cause an allergic reaction such as a gastrointestinal disorder, dizziness or other allergic reaction, or a systemic allergic reaction similar to these allergic reactions.

In the present disclosure, "pharmaceutically acceptable carrier", includes, but is not limited to, binders (such as microcrystalline cellulose, alginates, gelatin and polyvinylpyrrolidone), fillers (such as starch, sucrose, glucose and anhydrous lactic acid), disintegrants (such as cross-linked PVP, cross-linked carboxymethyl sodium starch, croscarmellose sodium and low-substituted hydroxypropyl cellulose), lubricants (magnesium stearate, aluminum stearate, talc, polyethylene glycol, sodium benzoate), wetting agent (such as glycerin), surfactants (such as cetyl alcohol), and absorption enhancers, flavoring agents, sweeteners, diluents, coating agents, etc.

The disease as described above is one or more selected from the group consisting of airway inflammation, asthma, bronchial asthma, allergic asthma, chronic obstructive pulmonary disease, idiopathic pulmonary fibrosis, rheumatoid arthritis, osteoarthritis, ankylosing spondylitis, psoriatic arthritis, psoriasis, multiple sclerosis, systemic sclerosis, systemic lupus erythematosus, lupus nephritis, scleroderma, ulcerative colitis, inflammatory bowel disease, uveitis, *Helicobacter pylori*-associated gastritis, osteoporosis, bone erosion, intraperitoneal abscess and adhesions, Addison's disease, gamma globulin deficiency, alopecia areata, celiac disease, Chagas disease, Crohn's disease, allograft rejection, Behcet's disease, sepsis, septic or endotoxin shock and ischemia.

A method of preventing and/or treating a disease associated with overexpression and/or over-release of IL-17A, comprising administering the drug as described above to a subject in need thereof.

Preferably, the above-mentioned individual is a human being, and further, the above-mentioned individual is a human being in need of preventing and/or treating of a disease associated with overexpression and/or over-release of IL-17A.

The disease as described above is one or more selected from the group consisting of airway inflammation, asthma, bronchial asthma, allergic asthma, chronic obstructive pulmonary disease, idiopathic pulmonary fibrosis, rheumatoid arthritis, osteoarthritis, ankylosing spondylitis, psoriatic arthritis, psoriasis, multiple sclerosis, systemic sclerosis, systemic lupus erythematosus, lupus nephritis, scleroderma, ulcerative colitis, inflammatory bowel disease, uveitis, *Helicobacter pylori*-associated gastritis, osteoporosis, bone erosion, intraperitoneal abscess and adhesions, Addison's disease, gamma globulin deficiency, alopecia areata, celiac disease, Chagas disease, Crohn's disease, allograft rejection, Behcet's disease, sepsis, septic or endotoxin shock and ischemia.

BRIEF DESCRIPTION OF DRAWINGS

In order to more clearly illustrate the specific embodiments of the present disclosure or the technical solutions in the conventional art, the drawings used in the specific embodiments or the description of the conventional art will be briefly described below, and it is obvious that the drawings in the following description are some embodiments of the present disclosure and a person having ordinary skill in the art can obtain other drawings based on these drawings without any creative work.

DETAILED DESCRIPTION

Figure 1:
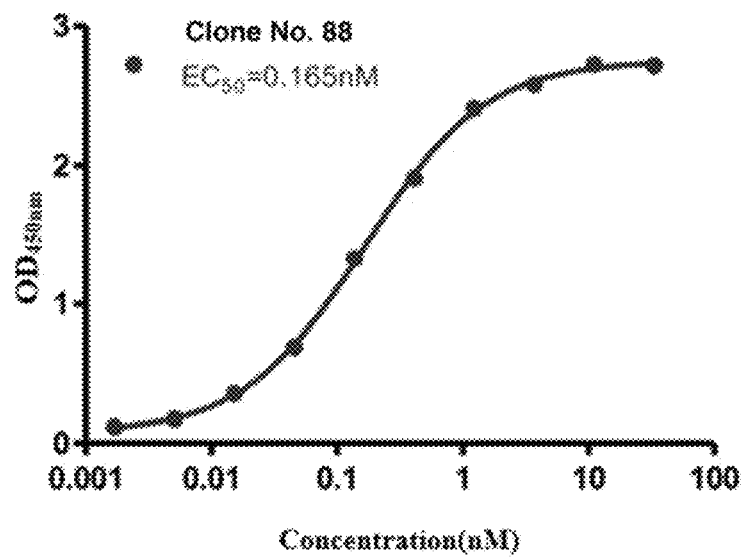
FIG. 1 shows the human IL-17A binding activity of the monoclonal antibody secreted by Clone No. 88 in Example 1.

The embodiments of the present disclosure will be described in detail below with reference to the embodiments. However, a person having ordinary skill in the art will understand that the following embodiments are merely to illustrate present disclosure and are not intended to limit the scope of the disclosure. For those embodiments in which specific conditions are not specified, they were carried out according to the conventional conditions or the conditions recommended by the manufacturer. For those used reagents or instruments of which the manufacturers are not indicated, they were all commercially available conventional products.

Example 1. Preparation of Murine Anti-Human IL-17A Monoclonal Antibody 1.1. Immunization of Animal Female BALB/c mice, 6 to 8 weeks old, purchased from Beijing Huafukang Biotechnology Co., Ltd., were used as experimental animals. One week after the mice were acclimated to the environment, immunization began. The recombinant human IL-17A protein was expressed in *E. coli*, and the inclusion bodies were collected and subjected to denaturation and refolding treatment to obtain soluble IL-17A protein. For the initial immunization, 100 µg of recombinant human IL-17A-Fc protein was thoroughly mixed with Freund's complete adjuvant (Sigma-Aldrich, Catalog Number F5881) to form an emulsion, which was intraperitoneally injected into the mice. Two weeks later, booster immunizations were performed. For the booster immunization, 50 µg of recombinant human IL-17A-Fc protein was thoroughly mixed with Freund's incomplete adjuvant (Sigma-Aldrich, Catalog Number F5806) to form an emulsion, which was intraperitoneally injected into the mice. The immunization was boosted in the same way every 2 weeks, for a total 3 times. On the seventh day after the last immunization, blood was collected from retro orbital venous plexus of the mice and centrifuged to separate serum, and the antibody titer was determined by ELISA. Mice with high titers were selected for hybridization to make hybridomas. Three days before the hybridization, 50 µg of recombinant human IL-17A-Fc protein was intraperitoneally injected into mice without adjuvant. On the day of hybridization, the spleen was aseptically removed to prepare a single spleen cell suspension for use.

1.2. Preparation of Hybridomas

Myeloma cells SP2/0 in logarithmic growth phase were centrifuged at 1000 rpm for 5 minutes, the supernatant was discarded, and the cells were suspended in incomplete DMEM medium (Gibco, cat No. 11965) and counted. The cells needed were taken, washed twice with an incomplete culture medium. At the same time, a spleen cell suspension prepared from a mouse after immunization was washed twice with an incomplete culture medium. The myeloma cells and the spleen cells were mixed at a ratio of 1:10 or 1:5, and washed once with an incomplete culture medium in a 50 mL plastic centrifuge tube, and then centrifuged at 1200 rpm for 8 minutes. The supernatant was discarded and a Pasteur pipette was used to remove residual liquid. The centrifuge tube was gently tapped on palm to make the precipitated cells loose and even, and then the tube was placed in 40° C. water bath to preheat. 1 mL of 45% PEG-4000 (pH 8.0, Sigma, cat No. P7181) preheated to 40° C. was added with 1 mL pipette at about 1 minute (with an optimum time of 45 seconds), stirred gently with a pipette when adding (stirred with a pipette), visible particles should be seen with the naked eyes. 20 to 30 mL of incomplete medium preheated to 37° C. was added to the tube with 10 mL pipette within 90 seconds to terminate PEG action, and allowed to stand at 20 to 37° C. for 10 minutes. The tube was centrifuged at 1000 rpm for 5 minutes, and the supernatant was discarded. 5 mL of HAT medium (DMEM+HAT, Sigma, cat No. 1 H0262-10VL) was added, and the precipitated cells were mixed gently (remember not to blow vigorously so as not to separate the fused cells) to make a well mixed suspension. Additional HAT medium was added until 80 to 100 mL (the spleen cell concentration was made to be 1 to $2\times10^6$/mL). The suspension was dispensed into a 96-well cell culture plate, 0.1 mL per well; and a 24-well plate, 1.0 to 1.5 mL per well. The plates were incubated at 37° C. incubator with 6% $CO_2$. Generally, six 96-well plates were used. After 5 days, ½ medium was replaced with fresh HAT medium. After 7 to 10 days, the HAT medium was replaced with HT medium (DMEM+HT, Sigma cat No. H0137-10VL). The growth of hybridoma cells was observed routinely, and the supernatant was collected for antibody detection after the confluence of the cells reached 1/10 or more. The positive colonies were expanded and frozen.

1.3. Clone Screening and Identification

ELISA was used to screen anti-human IL-17A antibody from hybridoma culture supernatants. Recombinant human IL-17A was coated on a 96-well high-absorbing ELISA plate with a carbonate buffer solution with pH 9.6, the coating concentration was 1 µg/mL, the coating amount was 100 µL per well, and the coating was carried out at 4° C. overnight. The plate was washed five times with PBST, blocked with 300 µL/well of PBST containing 1% BSA, and then incubated at 25° C. for 1 hour. The plate was washed five times with PBST. 100 µL culture supernatant samples and the positive serum control were added to each well respectively, and then the plated was incubated at 25° C. for 1 hour. The plate was washed five times with PBST. Then, 100 µL horseradish peroxidase-labeled anti-mouse IgG antibody (Abcam, Catalog Number Ab7068) 1:10000 diluted in PBST containing 1% BSA was added to each well, and then the plated was incubated at 25° C. for 1 hour. The plate was washed five times with PBST. 100 µL/well of colorimetric substrate TMB was added and incubated at room temperature for 10 minutes. Color development was terminated by adding 100 µL/well of 1 M $H_2SO_4$. The absorbance at 450 nm was read on a microplate reader. Positive clones capable of producing anti-human IL-17A antibody were selected based on the reading value at OD 450 nm.

Whether anti-human IL-17A antibody secreted by positive clone was a neutralizing antibody was determined by cell assays. The anti-human IL-17A antibody sample was diluted in DMEM complete medium (GIBCO, Catalog Number 11995-073) containing 10% FBS (Hyclone, Catalog Number SH30084.03). The starting concentration of the antibody was 160 nM and the final concentration was 40 nM in the medium. The antibody was subjected to 5 fold serial dilution, and then added to a cell culture plate, 50 µL per well. 20 ng/mL of human IL-17A (final concentration 5 ng/mL) was diluted with the same complete medium and added to the cell culture plate at 50 µL per well. The plate was incubated at 37° C. for 1 hour in an incubator with 5% $CO_2$. The HFF-1 cells were resuspended in complete medium and seeded into a 96-well cell culture plate at 100 µL per well, 5000 cells per well. The cells were incubated at 37° C. for 24 hours in an incubator with 5% $CO_2$. After the completion of the incubation, the cell culture plate was centrifuged at 250×g for 5 minutes, and the culture supernatant was removed, and the human IL-6 level was detected using human IL-6 ELISA kit (R&D systems, Catalog Number S6050) according to the instructions. The antibody capable of inhibiting the human IL-17A-stimulated secretion of human IL-6 by HFF-1 cells was anti-human IL-17A neutralizing antibody. Positive clone capable of secreting anti-human IL-17A neutralizing antibody was selected based on the strength of neutralization.

Figure 2:
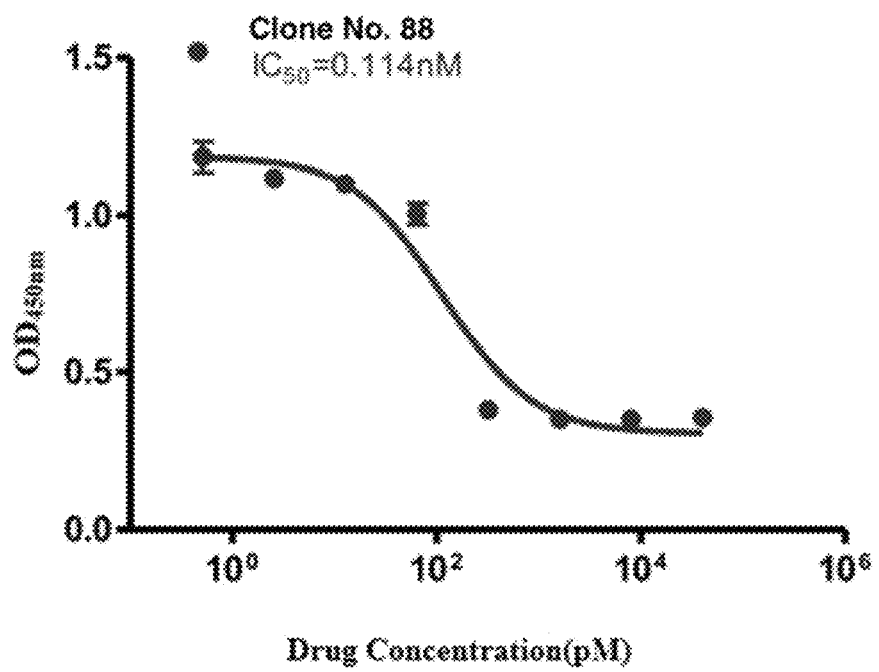
FIG. 2 shows the neutralization activity of the monoclonal antibody secreted by Clone No. 88 in Example 1 against human IL-17A-stimulated secretion of IL-6 by HFF-1 cells.

The result is shown in FIG. 1. Clone No. 88 has a strong human IL-17A binding activity. According to what is shown in FIG. 2, Clone No. 88 also has pretty strong human IL-17A neutralization activity.

1.4. Sequencing of Monoclonal Antibody

The clones having both antigen-binding activity and antigen-neutralization activity obtained by screening were subjected to sequencing of antibody DNA sequence. Cellular mRNA was first extracted using RNAprep Pure Kit (Tiangen, DP430). The steps were as follows: $1 \times 10^7$ cells were centrifuged at 300×g for 5 minutes and collected into a centrifuge tube, and all supernatant was carefully aspirated. The lysis step was carried out immediately. The bottom of the centrifuge tube was flicked to loose the cell pellet, 600 µL of lysis buffer RL was added with vortex. All solution was transferred to a filtration column CS (the filtration column CS was placed in a collection tube), centrifuged at 12,000 rpm (~13,400×g) for 2 minutes, and the filtrate was collected. One fold volume of 70% ethanol (usually 350 µL or 600 µL) was added to the filtrate, well mixed, the obtained solution and precipitate were transferred into an adsorption column CR3 (the adsorption column CR3 was put into a collection tube), centrifuged at 12,000 rpm (~13,400×g) for 30 to 60 seconds, the liquid waste in the collection tube was removed, the adsorption column CR3 was put back into the collection tube. 350 µL of deproteinized solution RW1 was added to the adsorption column CR3, centrifuged at 12,000 rpm (~13,400×g) for 30 to 60 seconds, the liquid waste in the collection tube was removed, the adsorption column CR3 was put back into the collection tube. 80 µL of DNase I working solution was added to the center of the adsorption column CR3 and the column CR3 was allowed to stand at room temperature for 15 minutes. 350 µL of deproteinized solution RW1 was added to the adsorption column CR3, centrifuged at 12,000 rpm (~13,400×g) for 30 to 60 seconds, the liquid waste in the collection tube was removed, the adsorption column CR3 was put back into the collection tube. 500 µL of rinsing solution RW was added to the adsorption column CR3 (checked whether ethanol had been added before use), the column CR3 was allowed to stand at room temperature for 2 minutes, centrifuged at 12,000 rpm (~13,400×g) for 30 to 60 seconds, the liquid waste in the collection tube was removed, the adsorption column CR3 was put back into the collection tube. The column CR3 was centrifuged at 12,000 rpm (~13,400×g) for 2 minutes, and the waste was removed. The adsorption column CR3 was left at room temperature for a few minutes to let the residual rinsing solution in the adsorbent material thoroughly dry. The adsorption column CR3 was transferred into a new RNase-Free centrifuge tube, 30 to 100 µL of RNase-Free $ddH_2O$ was added, the tube was allowed to stand at room temperature for 2 minutes, and then centrifuged at 12,000 rpm (~13,400×g) for 2 minutes to obtain a RNA solution.

The first strand of cDNA was synthesized using the QuantScript RT kit (Tiangen, KR103). The steps are as follows: the template RNA was thawed on ice; the primer, 10×RT mix (containing RNasin and DTT), Super pure dNTP mixture, RNase-Free $ddH_2O$ were thawed at room temperature (15 to 25° C.), and placed on ice immediately after thawing. Each solution was well mixed by vortexer before use, the tube was centrifuged briefly to collect residual liquid on the side of the tube. Reverse transcription system mixture (Tiangen Bio Quant cDNA First-Strand Synthesis Kit, Catalog Number KR103-04; 10× Reverse Transcription Buffer 2 µL, Ultra-Pure dNTP 2 µL, Random Primer 2 µL, Reverse Transcription Enzyme 1 µL) was prepared according to Table 1. The mixture was mixed thoroughly, the duration of vortex was no more than 5 minutes; and then centrifuged briefly and placed on ice. Finally, the template RNA (50 ng to 2 µg) was added to the mixture, mixed thoroughly, the duration of vortex was no more than 5 seconds, centrifuged briefly to collect residual liquid on the sides of the tube, incubated at 37° C. for 60 minutes. The first strand of cDNA produced by reverse transcription was used for subsequent PCR reaction.

The primers used in the PCR reaction are shown in Table 1.

TABLE 1

PCR Primers

VH primer
F1: GAGGTGAAGCTGCAGGAGTCAGGACCTAGCCTGGTG

R1: AGGT(C/G)(A/C)AACTGCAG(C/G)AGTC(A/T)GG

R2: AGGT(C/G)(A/C)AGCTGCAG(C/G)AGTC(A/T)GG

R3: AGGT(C/G)CAGCTGCAG(C/G)AGTC(A/T)GG

R4: CCAGGGGCCAGTGGATAGACAAGCTTGGGTGTCGTTTT

F2: ATAGACAGATGGGGGTGTCGTTTTGGC

F3: CTTGACCAGGCATCCTAGAGTCA

F4: AGGGGCCAGTGGATAGACTGATGG

F5: AGGGACCAAGGGATAGACAGATGG

R5: (G/C)A(A/G)GT(A/T/C/G)(A/C)AGCTG(G/C)AG(G/C)AGTC

R6: (G/C)A(A/G)GT(A/T/C/G)(A/C)AGCTG(G/C)AG(G/C)AGTC(A/T)GG

VL primer
R1: GGTGATATCGTGAT(A/G)AC(C/A)CA(G/A)GATGAACTCTC

R2: GGTGATATC(A/T)TG(A/C)TGACCCAA(A/T)CTCCACTCTC

TABLE 1-continued

PCR Primers

R3: GGTGATATCGT(G/T)CTCAC(C/T)CA(A/G)TCTCCAGCAAT

F1: GGGAAGATGGATCCAGTTGGTGCAGCATCAGC

F2: GGATACAGTTGGTGCAGCATC

R4: GA(C/T)ATTGTG(A/C)T(G/C)AC(A/C)CA(A/G)(A/T)CT(A/C)CA

When primers were used, any upstream primer of the VH primers could be used with any downstream primer; in the same way, any upstream primer of the VL primers could also be used with any downstream primer. The target band obtained by PCR amplification was cloned into the pGEM-T vector. A single clone was picked for DNA sequencing.

Example 2. Preparation of Chimeric Anti-Human IL-17A Monoclonal Antibody

The nucleic acid sequence encoding the above mentioned antibody light chain (the full-length of the light chain was SEQ ID NO: 7 linked to SEQ ID NO: 9) and the heavy chain (the full-length of the heavy chain was SEQ ID NO: 8 linked to SEQ ID NO: 10) was cloned into a eukaryotic expression vector XOGC (wherein the full-length nucleic acid sequence of the light chain of the antibody is set forth in SEQ ID NO: 23, the full-length nucleic acid sequence of the heavy chain of the antibody is set forth in SEQ ID NO: 24), then the expression vector was transfected into a 293F cell line (FreeStyle™ 293-F Cells, Catalog Number R79007, invitrogen). Cells were inoculated one day prior to transfection. Cells were harvested by centrifugation on the day of transfection. The cells were resuspended in fresh FreeStyle™ 293 Expression Medium (FreeStyle™ 293 Expression Medium, Catalog Number 12338001, Gibco), the cell density was $200\times10^5$ cells/mL. Plasmid was added according to the transfection volume, the final concentration was 36.67 μg/mL, mixed gently; then linear PEI (polyethyleneimine, linear, M.W. 25000, Catalog Number 43896, Alfa Aesar) was added, the final concentration was 55 μg/mL, mixed gently. Thereafter, the cells were placed in a 120 rpm shaker and incubated at 37° C. for 1 hour. A 19-fold transfection volume of fresh medium was then added. Continued to incubate at 37° C. on a 120 rpm shaker. The cell culture supernatant transfected for 5 to 6 days was collected by centrifugation.

The amino acid sequence of the light chain variable region of the antibody obtained by PCR amplification is set forth in SEQ ID NO: 7, and the amino acid sequence of the heavy chain variable region of antibody is set forth in SEQ ID NO: 8. The sequence of the complementarity-determining region can be obtained by excluding the sequence of the framework region from the mouse variable region sequence; wherein the amino acid sequences of the three complementarity-determining regions CDR-L1, CDR-L2, CDR-L3 of the light chain are set forth in SEQ ID NO: 1, 2 and 3, respectively; the amino acid sequences of the three complementarity-determining regions CDR-H1, CDR-H2, CDR-H3 of the heavy chain are set forth in SEQ ID NO: 4, 5 and 6, respectively. The amino acid sequence of the light chain constant region of the antibody is set forth in SEQ ID NO: 9, and the amino acid sequence of the heavy chain constant region of the antibody is set forth in SEQ ID NO: 10. The nucleic acid sequence encoding the above mentioned antibody light chain (the full-length of the light chain was SEQ ID NO: 7 linked to SEQ ID NO: 9) and the heavy chain (the full-length of the heavy chain was SEQ ID NO: 8 linked to SEQ ID NO: 10) were cloned into eukaryotic expression vector XOGC (wherein the full-length nucleic acid sequence of the light chain of the antibody is set forth in SEQ ID NO: 23, the full-length nucleic acid sequence of the heavy chain of the antibody is set forth in SEQ ID NO: 24), then the expression vector was transfected into 293F cell line (FreeStyle™ 293-F Cells, Catalog Number R79007, Invitrogen). Cells were subcultured one day prior to transfection. Cells On the day of transfection, cells were harvested by centrifugation and then resuspended in fresh FreeStyle™ 293 Expression Medium (FreeStyle™ 293 Expression Medium, Catalog Number 12338001, Gibco) at a density of $200\times10^5$ cells/mL. Plasmids were added based on the transfection volume to a final concentration of 36.67 μg/mL, mixed gently; then linear PEI (polyethyleneimine, linear, M.W. 25000, Catalog Number 43896, Alfa Aesar) was added to a final concentration of 55 μg/mL, mixed gently. Thereafter, the cells were placed in a shaker at 120 rpm and incubated at 37° C. for 1 hour. 19-fold transfection volume of fresh medium was then added and the cells were continually cultured at 37° C. in a shaker at 120 rpm. The culture supernatant 5 to 6 days after transfection was collected by centrifugation.

Example 3. Kinetics of the Binding of Chimeric Anti-Human IL-17A Monoclonal Antibody to Human IL-17A The kinetics of the binding of anti-human IL-17A chimeric monoclonal antibody to antigen human IL-17A was detected using Biacore 3000 Instrument. The instrument utilizes an optical surface plasmon resonance technique to detect association and dissociation between a molecule coupled on a sensor chip and an analyte. CM5 chips (GE Healthcare, BR-1000-12) were used. Brief experiment procedure was as follow: human IL-17A was dissolved in sodium acetate buffer (pH 5.0) and coupled to CM chip by injecting at a speed of 10 μL/min. 1 M ethanolamine was injected at a speed of 10 μL/min for blocking. In the association phase, different concentrations of anti-human IL-17A chimeric monoclonal antibody and control were respectively injected at a speed of 30 μL/min for 180 seconds, and during the dissociation phase, PBS buffer was injected at a speed of 30 μL/min for 600 seconds. 10 mM glycine solution (pH 2.0) was used for regeneration. Association rate constants and dissociation rate constants were analyzed and calculated by Biacore 3000 control software. The association rate constant, dissociation rate constant and dissociation equilibrium constant of the anti-human IL-17A chimeric antibody are shown in Table 2. Compared with Secukinumab, the anti-human IL-17A mAb has smaller dissociation equilibrium constant, stronger affinity, especially after binding to IL-17A antigen, it could maintain the binding state for a longer time and is not easy to be dissociated, which contributes to its biological functions.

TABLE 2

Binding Kinetics of Anti-Human IL-17A Chimeric Antibody to Human IL-17A

| Sample Detected | $K_{on}$ (1/Ms) | $K_{off}$ (1/s) | $K_D$ (nM) |
| --- | --- | --- | --- |
| Secukinumab | 2.52E+05 | 7.96E−05 | 0.32 |
| Anti-human IL-17A Chimeric Antibody | 5.41E+04 | 1.49E−06 | 0.03 |

Example 4. Species Specificity and Binding Specificity of Chimeric Anti-Human IL-17A Monoclonal Antibody The species specificity of the anti-human IL-17A chimeric monoclonal antibody was determined by ELISA. Recombinant human IL-17A, monkey IL-17A, rat IL-17A and mouse IL-17A (all purchased from Sino Biological Inc.), were coated on a 96-well high-absorbing ELISA plate with a carbonate buffer solution with pH 9.6, the coating concentration was 1 g/mL, the coating amount was 100 μL per well, and the coating was carried out at 4° C. overnight. The plate was washed five times with PBST and blocked with 300 μL/well of PBST containing 1% BSA, and then incubated at 25° C. for 1 hour. The plate was washed five times with PBST. The control and the anti-human IL-17A chimeric monoclonal antibody sample serially diluted in PBST containing 1% BSA were added, 100 μL per well, incubated at 25° C. for 1 hour. The plate was washed five times with PBST. Then, horseradish peroxidase-labeled anti-human IgG antibody (Chemicon, Catalog Number AP309P) 1:2000 diluted in PBST containing 1% BSA was added, 100 μL per well, incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$. The absorbance at 450 nm was read on a microplate reader.

The binding specificity of the anti-human IL-17A chimeric monoclonal antibody was determined by ELISA. Recombinant human IL-17A, IL-17B, IL-17C, IL-17D, IL-17E, IL-17F, IL-1, IL-2, IL-6, IL-8, IL-21, IL-22, IL-23, IFN-g and TNFα (purchased from Sino Biological Inc. or R&D systems) were coated on a 96-well high-absorbing ELISA plate with a carbonate buffer solution with pH 9.6, the coating concentration was 1 μg/mL, the coating amount was 100 μL per well, and the coating was carried ax 4° C. out overnight. The plate was washed five times with PBST and blocked with 300 μL/well of PBST containing 1% BSA and incubated at 25° C. for 1 hour. The plate was washed five times with PBST. The control and the anti-human IL-17A chimeric monoclonal antibody sample diluted in PBST containing 1% BSA were added, 100 μL per well, incubated at 25° C. for 1 hour. The plate was washed five times with PBST. Then, horseradish peroxidase-labeled anti-human IgG antibody (Chemicon, Catalog Number AP309P) 1:2000 diluted in PBST containing 1% BSA was added, 100 μL was added to each well, incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$. The absorbance at 450 nm was read on a microplate reader.

The binding specificity of the anti-human IL-17A chimeric monoclonal antibody was determined by ELISA. Recombinant human IL-17A, IL-17B, IL-17C, IL-17D, IL-17E, IL-17F, IL-1, IL-2, IL-6, IL-8, IL-21, IL-22, IL-23, IFN-g and TNFα (purchased from Sino Biological Inc. or R&D systems) were coated on a 96-well high-absorbing ELISA plate with a carbonate buffer solution with pH 9.6, the coating concentration was 1 μg/mL, the coating amount was 100 μL per well, and the coating was carried at 4° C. out overnight. Washed five times with PBST. Blocked with 300 μL/well of PBST containing 1% BSA and incubated at 25° C. for 1 hour. Washed five times with PBST. The control and the anti-human IL-17A chimeric monoclonal antibody sample diluted in PBST containing 1% BSA were added, 100 μL was added to each well, incubated at 25° C. for 1 hour. Washed five times with PBST. Then, horseradish peroxidase-labeled anti-human IgG antibody (Chemicon, Catalog Number AP309P) 1:2000 diluted in PBST containing 1% BSA was added, 100 μL was added to each well, incubated at 25° C. for 1 hour. Washed five times with PBST. 100 μL/well of colorimetric substrate TMB was added, developed at room temperature for 10 minutes. Color development was terminated by adding 100 μL/well of 1 M $H_2SO_4$. The absorbance at 450 nm was read on a microplate reader.

Figure 3:
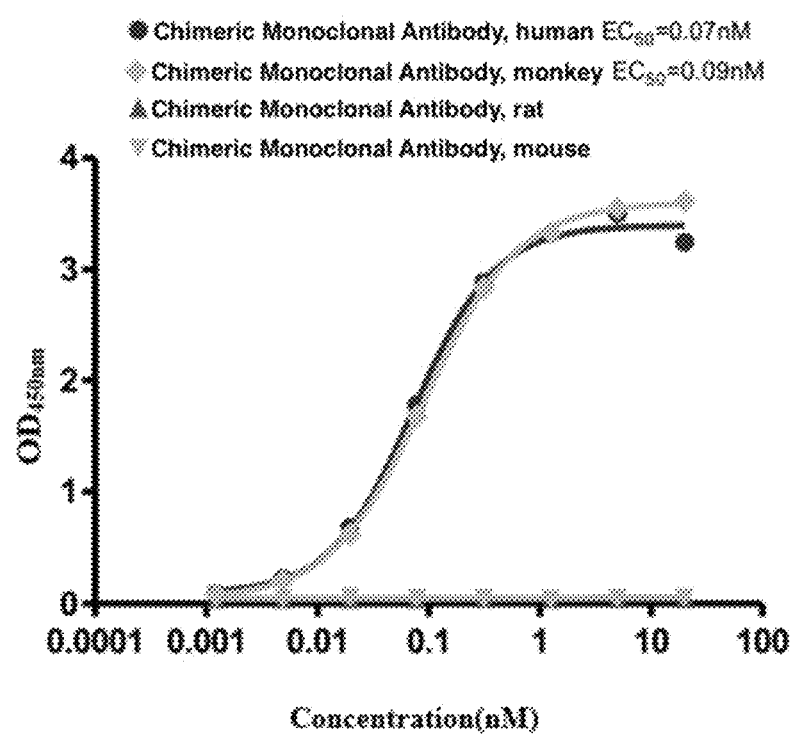
FIG. 3 shows the species specificity of the anti-human IL-17A chimeric monoclonal antibody in Example 4.
Figure 4:
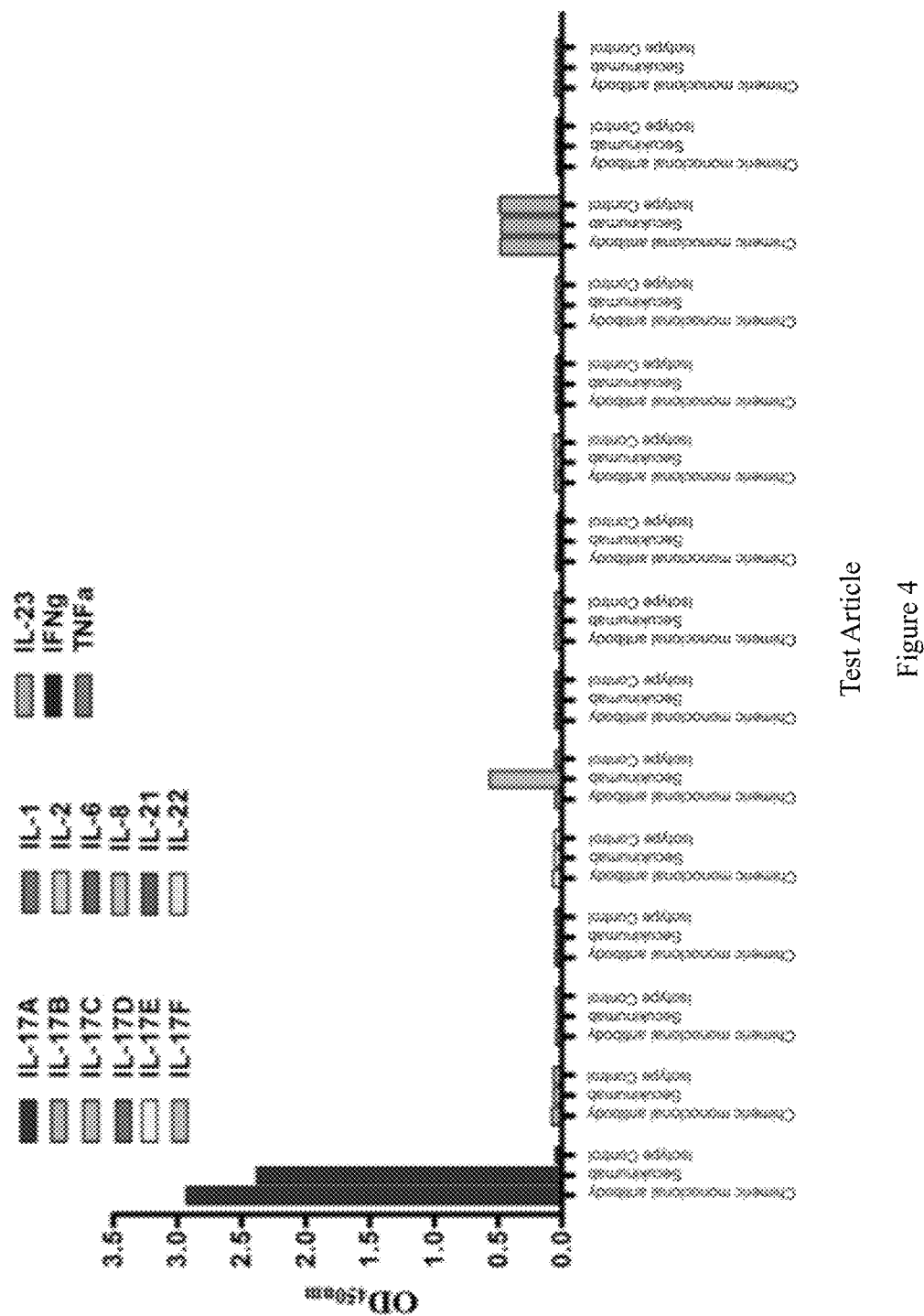
FIG. 4 shows the binding specificity of the anti-human IL-17A chimeric monoclonal antibody in Example 4.

The result is shown in FIG. 3. The anti-human IL-17A chimeric monoclonal antibody bound to human and monkey IL-17A, but not rat or mouse IL-17A, indicating the antibody was species-specific. In addition, as shown in FIG. 4, the anti-human IL-17A chimeric monoclonal antibody also has strong binding specificity, which only bound to IL-17A but not other cytokines of IL-17 family or unrelated cytokines.

Example 5. Neutralization Activity of Chimeric Anti-Human IL-17A Monoclonal Antibody In Vitro The anti-human IL-17A antibody sample was diluted in DMEM complete medium (GIBCO, Catalog Number 11995-073) containing 10% FBS (Hyclone, Catalog Number SH30084.03). The starting concentration of the antibody was 160 nM and the final concentration was 40 nM in the medium. The antibody was subjected to 5 fold serial dilution, and then added to a cell culture plate, 50 μL per well. 20 ng/mL of human IL-17A (final concentration 5 ng/mL) was diluted with the same complete medium and added to the cell culture plate at 50 μL per well. The plate was incubated at 37° C. for 1 hour in an incubator with 5% $CO_2$. The HFF-1 cells were resuspended in complete medium and seeded into a 96-well cell culture plate at 100 μL per well, 5000 cells per well. The cells were incubated at 37° C. for 24 hours in an incubator with 5% $CO_2$. After the completion of the incubation, the cell culture plate was centrifuged at 250×g for 5 minutes, and the culture supernatant was removed, and the human IL-6 level was detected using human IL-6 ELISA kit (R&D systems, Catalog Number S6050) according to the instructions.

Figure 5:
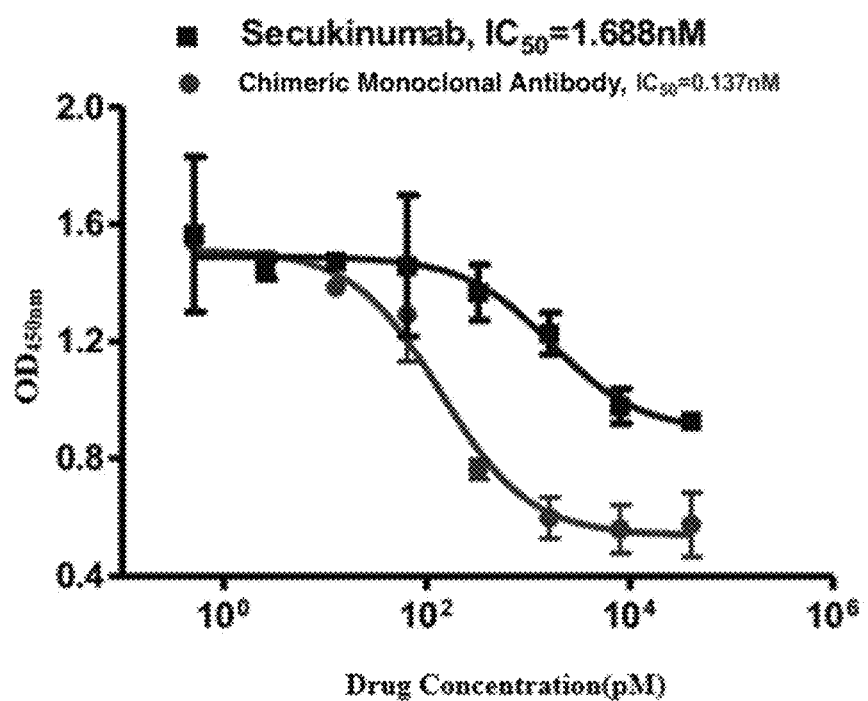
FIG. 5 shows the in vitro neutralization activity of the anti-human IL-17A chimeric monoclonal antibody in Example 5.

The result is shown in FIG. 5. Compared to Secukinumab, the anti-human IL-17A chimeric monoclonal antibody has a stronger IL-17A neutralization activity in vitro, and a better effect on inhibiting the human IL-17A-stimulated secretion of human IL-6 by HFF-1 cells.

Example 6. Neutralization Activity of Chimeric Anti-Human IL-17A Monoclonal Antibody In Vivo Female BALB/c mice, 6 to 8 weeks old, purchased from Beijing Huafukang Biotechnology Co., Ltd., were used as experimental animals. One week after the mice were acclimated to the environment, the mice were randomly divided into groups, 6 per group. Each group was given anti-human IL-17A chimeric monoclonal antibody or control monoclonal antibody Secukinumab, at three doses of 0.7 nmol/kg, 7 nmol/kg or 70 nmol/kg, intravenous injection, single administration. One hour after the administration, human IL-17A was injected subcutaneously, 10 μg per mouse. Two hours later, retro-orbital blood sample was collected without anticoagulation, and the blood sample was allowed to stand at room temperature for 30 minutes to 1 hour. After the coagulation of blood, the sample was centrifuged at 3000 rpm for 10 minutes to obtain a serum sample. The concentration of mouse CXCL1 (C-X-C Motif Chemokine Ligand, also known as KC) in the serum was detected according to the instructions using a mouse CXCL1 ELISA kit (RayBiotech, Catalog Number ELM-KC).

Figure 6:
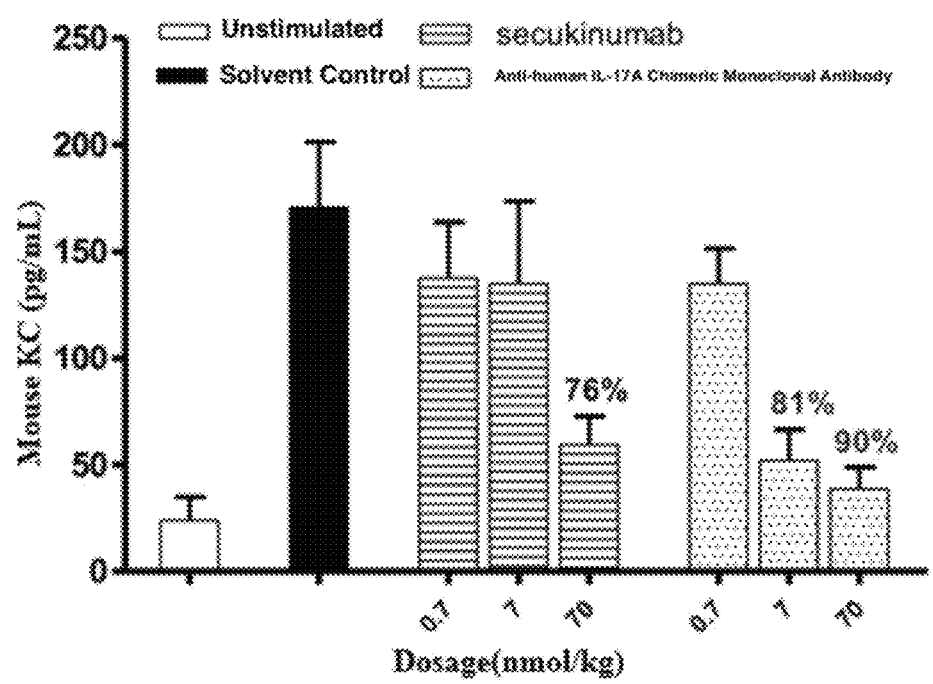
FIG. 6 shows the in vivo neutralization activity of the anti-human IL-17A chimeric monoclonal antibody in Example 6.

The result is shown in FIG. 6. The anti-human IL-17A chimeric monoclonal antibody inhibited the secretion of CXCL1 in human IL-17A-stimulated mice, showing a stronger activity than the control monoclonal antibody Secukinumab.

Example 7. Pharmacokinetics Study of Chimeric Anti-Human IL-17A Monoclonal Antibody in Rats Female SD rats, 6 to 8 weeks old, purchased from Beijing Huafukang Biotechnology Co., Ltd., were used as experimental animals. One week after the rats were acclimated to the environment, the rats were randomly divided into groups, 3 rats per group. Anti-human IL-17A chimeric monoclonal antibody and control monoclonal antibody Secukinumab were administered respectively at a dose of 20 nmol/kg by intravenous injection, single dose. At 0, 5 minutes, 30 minutes, 1 hour, 4 hours, 8 hours, 24 hours, 48 hours, 72 hours, 96 hours, 120 hours, 168 hours, 216 hours, 264 hours, 312 hours after administration, the retro-orbital blood sample was collected without anticoagulation, and the blood sample was allowed to stand at room temperature for 30 minutes to 1 hour; after coagulation, the blood sample was centrifuged at 3,000 rpm for 10 minutes, the obtained serum sample was frozen at −80° C. and stored for testing.

The concentrations of anti-human IL-17A chimeric monoclonal antibody and control monoclonal antibody Secukinumab in the serum were determined by ELISA. Briefly, human recombinant IL-17A protein was coated on a high-absorbing ELISA plate with a carbonate buffer solution with pH 9.6 at 4° C. overnight. The plate was washed with PBST. To prevent non-specific binding, the plate was blocked with PBST containing 5% nonfat milk powder, and then washed with PBST. Then, the serum sample to be tested diluted with PBST containing 10% mixed rat serum and 1% BSA was added and incubated at 25° C. for 1 hour, and the plate was washed with PBST. Horseradish peroxidase-labeled anti-human IgG antibody (Chemicon, Catalog Number AP309P) diluted in PBST containing 5% skimmed milk powder was added, incubated at 25° C. for 1 hour, the then plate was washed with PBST. Finally, color development was carried out using the colorimetric substrate TMB at room temperature for 10 minutes. Color development was terminated by adding 100 μL/well of 1 M $H_2SO_4$. The absorbance at 450 nm was read on a microplate reader.

Figure 7:
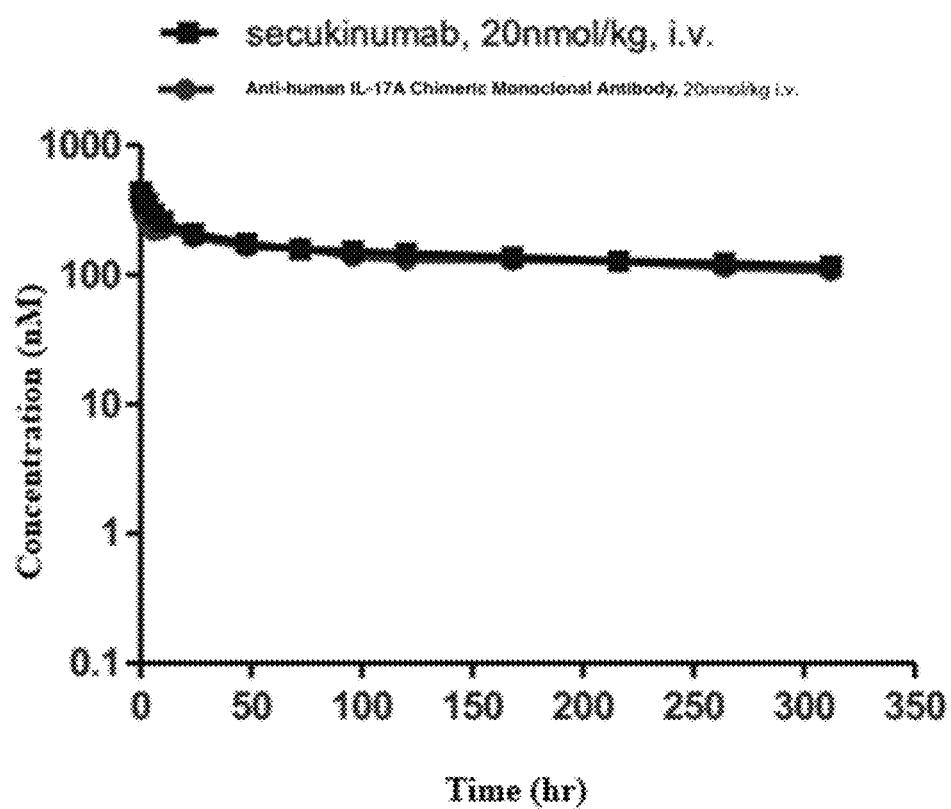
FIG. 7 shows the concentration-time curve after the single intravenous injection in Example 7.

The result is shown in FIG. 7. A single intravenous injection dose of 20 nmol/kg of anti-human IL-17A chimeric monoclonal antibody or control monoclonal antibody Secukinumab showed similar concentration-time curves and pharmacokinetic features in rats. The pharmacological parameters of the anti-human IL-17A chimeric monoclonal antibody are as follows: half-life $t_{1/2}$ was 458 hours; the area under the concentration-time curve $AUC_{last}$ was 44,286 nM·hr; the estimated initial concentration Co was 413 nM; the apparent volume of distribution Vd was 115 mL/kg, the clearance rate CL was 0.17 mL/hr/kg; the mean residence time $MRT_{last}$ was 140 hours.

Example 8. Preparation of Humanized Anti-Human IL-17A Monoclonal Antibody

The humanized form of the anti-IL-17 antibody was obtained according to the method of Leung et al. (1995, Molecule Immunol 32: 1413-27).

The humanized template that best matches murine non-CDR region was selected from Germline database. The template for the heavy chain variable region was IGVH4-59*01 and the sequence is set forth in SEQ ID NO: 35. The template for the light chain variable region was IGKV2-30*02 and the sequence is set forth in SEQ ID NO: 36. The CDR region of murine antibody was grafted onto the selected humanized template, replacing the CDR region of the human template. The obtained grafted humanized antibody heavy chain variable region has a sequence set forth in SEQ ID NO: 37, and the grafted humanized antibody light chain variable region has a sequence set forth in SEQ ID NO: 38. Nine positions selected by sequence alignment were subjected to back mutations, including 4 positions on heavy chains: L4V, I49M, V68I, V72R, and 5 positions on light chains: D1I, V2I, F41Y, R51L, Y92F. Different humanized sequences were constructed by reducing the number of back mutations, and the heavy chain sequences and the light chain variable region sequences are shown in Table 3. The heavy chain variable region (SEQ ID NO: 27-34) of the humanized anti-human IL-17A monoclonal antibody was linked to the heavy chain constant region (SEQ ID NO: 10) of human antibody IgG1 to obtain corresponding full-length sequence of heavy chain. The light chain variable region (SEQ ID NO: 19-26) of the humanized anti-human IL-17A monoclonal antibody was linked to the light chain constant region (SEQ ID NO: 9) of the human Kappa antibody to obtain corresponding full-length sequence of light chain. The full-length sequence of the heavy chain was combined with the full-length sequence of the light chain to obtain a full-length sequence of the humanized antibody. The full-length sequence was digested with EcoRI and HindIII, and then inserted into XOGC vector.

TABLE 3

The Sequences of the Heavy Chain Variable Region and Light Chain Variable Region of Anti-human IL-17A Humanized Antibody

| | SEQ ID NO: |
|---|---|
| VH | |
| Grafted | 27 |
| BM | 28 |
| AS15799 | 29 |
| AS15802 | 30 |
| AS15803 | 31 |
| AS15805/AS15815 | 32 |
| AS15810 | 33 |
| AS15820 | 34 |
| VL | |
| Grafted | 19 |
| BM | 20 |
| AS15799 | 21 |
| AS15802/AS15803 | 22 |
| AS15805 | 23 |

TABLE 3-continued

The Sequences of the Heavy Chain Variable Region and Light Chain Variable Region of Anti-human IL-17A Humanized Antibody

| | SEQ ID NO: |
|---|---|
| AS15810 | 24 |
| AS15815 | 25 |
| AS15820 | 26 |

Example 9. Antigen Binding Activity of Humanized Anti-Human IL-17A Monoclonal Antibody The antigen binding activity of humanized anti-human IL-17A monoclonal antibody was determined by ELISA. Recombinant human IL-17A (purchased from Sino Biological Inc.) was coated on a 96-well high-absorbing ELISA plate with a carbonate buffer solution with pH 9.6, the coating concentration was 1 μg/mL, the coating amount was 100 μL per well, and the coating was carried at 4° C. out overnight. The plate was washed five times with PBST and blocked with 300 μL/well of PBST containing 1% BSA and incubated at 25° C. for 1 hour. The plate was washed five times with PBST. The control and the anti-human IL-17A chimeric monoclonal antibody sample diluted in PBST containing 1% BSA were added, 100 μL per well, incubated at 25° C. for 1 hour. The plate was washed five times with PBST. Then, horseradish peroxidase-labeled anti-human IgG antibody (Chemicon, Catalog Number AP309P) 1:2000 diluted in PBST containing 1% BSA was added, 100 μL was added to each well, incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$. The absorbance at 450 nm was read on a microplate reader.

Figure 8:
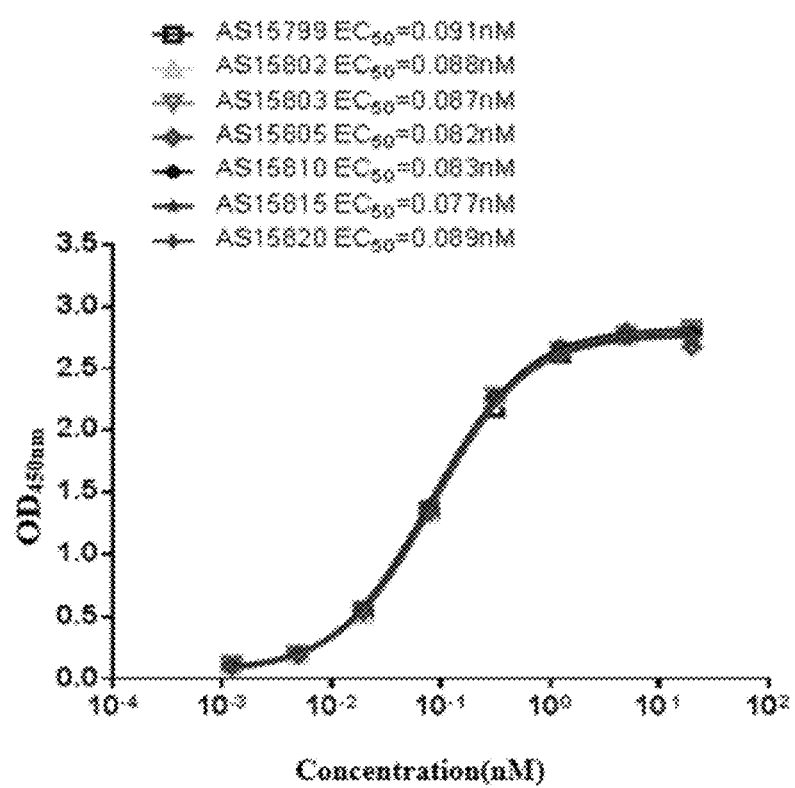
FIG. 8 shows the antigen binding activity of the anti-human IL-17A humanized monoclonal antibody in Example 9.

The result is shown in FIG. 8. All of the anti-human IL-17A humanized monoclonal antibodies AS15799, AS15802, AS15803, AS15805, AS15810, AS15815 and AS15820 could bind human IL-17A with a high affinity activity.

Example 10. Neutralization Activity of Humanized Anti-Human IL-17A Monoclonal Antibody In Vitro The anti-human IL-17A antibody sample was diluted in DMEM complete medium (GIBCO, Catalog Number 11995-073) containing 10% FBS (Hyclone, Catalog Number SH30084.03). The starting concentration of the antibody was 160 nM and the final concentration was 40 nM in the medium. The antibody was subjected to 5 fold serial dilution, and then added to a cell culture plate, 50 μL per well. 20 ng/mL of human IL-17A (final concentration 5 ng/mL) was diluted with the same complete medium and added to the cell culture plate at 50 μL per well. The plate was incubated at 37° C. for 1 hour in an incubator with 5% $CO_2$. The HFF-1 cells were resuspended in complete medium and seeded into a 96-well cell culture plate at 100 μL per well, 5000 cells per well. The cells were incubated at 37° C. for 24 hours in an incubator with 5% $CO_2$. After the completion of the incubation, the cell culture plate was centrifuged at 250×g for 5 minutes, and the culture supernatant was removed, and the human IL-6 level was detected using human IL-6 ELISA kit (R&D systems, Catalog Number S6050) according to the instructions.

Figure 9:
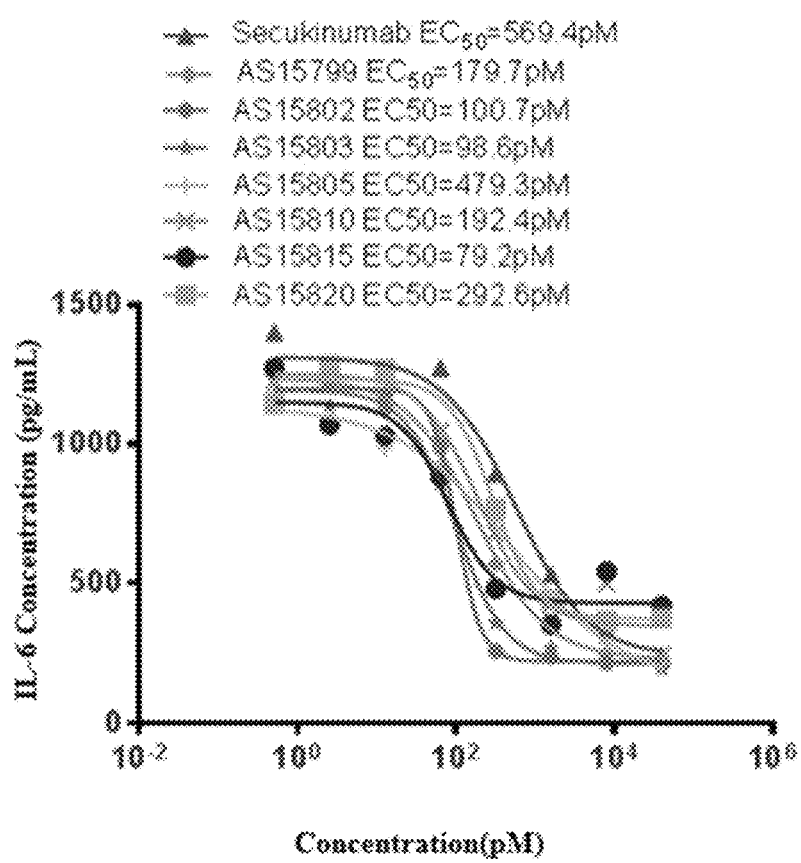
FIG. 9 shows the in vitro neutralization activity of the anti-human IL-17A humanized monoclonal antibody in Example 10.

The result is shown in FIG. 9. Compared to Secukinumab, anti-human IL-17A humanized monoclonal antibodies AS15799, AS15802, AS15803, AS15805, AS15810, AS15815 and AS15820 have stronger IL-17A neutralization activity and stronger effect on inhibiting the human IL-17A-stimulated secretion of human IL-6 by HFF-1 cells in vitro.

Example 11. Detection of Purity and Thermal Stability of Humanized Anti-Human IL-17A Monoclonal Antibody by Size-Exclusion High-Performance Liquid. Chromatography (SE-HPLC)

TSKgel SuperSW3000 chromatography column (Catalog Number: 0018675) was used. The mobile phase was 0.1 mol/l of phosphate buffer ($NaH_2PO_4$—$Na_2HPO_4$), 0.1 mol/l of sodium sulfate buffer, pH 6.7; the flow rate was 0.35 mL/min; the column temperature was 25° C.; sample pool temperature was 4° C.; detection wavelength was 280 nm. The sample was diluted with sample buffer to 1 mg/mL, and the injection volume was 5 μL. The experiment result was processed by Agilent High Performance Liquid Chromatograph 1260 System Workstation, and purity was calculated by the percentage of the main peak using area normalization method. The humanized anti-human IL-17A monoclonal antibody prepared above was subjected to SE-HPLC purity assay. To determine the thermal stability of these monoclonal antibodies, the samples were placed under high temperature conditions of 40° C., and the samples were subjected to SE-HPLC assay at week 2 and week 4 respectively to observe thermal stability, and the result is shown in Table 4 below. All of the humanized anti-human IL-17A antibodies showed good and considerable stability.

TABLE 4

Thermal Stability of Humanized Anti-human IL-17A Monoclonal Antibody at 40° C. by SE-HPLC

| Humanized Anti-human IL-17A Monoclonal Antibody | SE-HPLC Purity | | |
|---|---|---|---|
| | T = 0 | Week 2 | Week 4 |
| AS15802 | 99.9% | 98.5 | 97.3 |
| AS15803 | 99.9% | 98.3 | 96.9 |
| AS15810 | 98.0% | 96.9 | 95.9 |
| AS15815 | 98.1% | 97.2 | 96.5 |
| AS15820 | 96.5% | 95.7 | 94.5 |

Example 12. Determination of Tm Value of Humanized Anti-Human IL-17A Monoclonal Antibody The melting temperature (Tm) of the humanized anti-human IL-17A monoclonal antibody was determined by Differential Scanning Fluorimetry (DSF). DSF is a method for detecting the thermal denaturation process of proteins in a sample by using the fluorescence intensity change of the fluorescent indicator to determine the protein denaturation temperature. The reagent used was SYPRO Orange Protein Fluorescent Dye (Sigma-Aldrich, USA, Catalog Number S5692; 5000× concentration, in DMSO). AB 7500 Real Time PCR machine was purchased from Applied Biosystems, Inc., USA. The protein fluorescent dye was diluted 1:50 with sample buffer, and 1 μL of the diluted dye was mixed with 19 μL of protein solution, so the final dilution of the fluorescent dye was 1:1000. The diluted fluorescent dye was added to a 96-well plate, and three parallel wells were set for each sample. The plate was sealed with an optical sealing film, centrifuged at 1000 rpm for 2 minutes to remove air bubbles. The RT-PCR program was set as follows: melting curve was set in continuous mode, scanning temperature range was 25 to 99° C., heating rate was 1% (about 1° C./min), and then 25° C. for 2 min. Data was collected during heating, the reporter group was set as "ROX", the quenching group was set as "None", and the reaction volume was 20 μL. The sample concentration was 1 mg/mL, and the reference solution was sample buffer. Fluorescence curves and the first derivative were plotted using Protein Thermal Shift™ Software v1.3 software. In the DSF test, the midpoint temperature of the first transition of the protein is usually considered as the denaturation temperature of the thermal stability of the protein. The Tm values of the humanized anti-human IL-17A monoclonal antibody were measured and the result is shown in Table 5 below. All of the humanized anti-human IL-17A monoclonal antibodies have pretty good Tm value.

TABLE 5

Tm Value of Humanized Anti-human IL-17A Monoclonal Antibody

| Humanized Anti-human IL-17A Monoclonal Antibodies | Tm Value |
| --- | --- |
| AS15802 | 67.2° C. |
| AS15803 | 68.3° C. |
| AS15810 | 67.9° C. |
| AS15815 | 69.3° C. |
| AS15820 | 67.7° C. |

Example 13. Detection of Charge Isomers of Humanized Anti-Human IL-17A Monoclonal Antibody by Cation Exchange Chromatography (CEX)

Cation exchange chromatography column MabPac SCX-10 was used, 4 mm×250 mm (Catalog Number: 78655). 20 mmol/L of 2-(N-morpholine) ethanesulfonic acid (MES) (pH 5.6) and 60 mmol/L of sodium chloride were used as mobile phase A; 20 mmol/L of MES (pH 5.6) and 300 mmol/L of sodium chloride were used as mobile phase B. The flow rate was 0.5 mL/min; the column temperature was 25° C.; sample pool temperature was 4° C.; detection wavelength was 280 nm; the sample loading volume was 50 μL (1 mg/mL); the elution was carried out in a linear gradient from 5 to 50% over 60 minutes. The experiment result was processed by Agilent High Performance Liquid Chromatograph 1260 System Workstation, and the percentage of the peak area was calculated by the area normalization method. The humanized anti-human IL-17A monoclonal antibodies were subjected to CEX detection. To determine the chemical stability of these monoclonal antibodies, the above samples were put under high temperature conditions of 40° C., and the samples were taken out at week 2 and week 4 respectively for CEX detection and the changes in the proportion of charge variants was observed. The result is shown in Table 6. All of the humanized anti-human IL-17A antibodies have a relatively low proportion of charge variants.

TABLE 6

Changes in Charge Variants of Humanized Anti-human IL-17A Monoclonal Antibody at 40° C. by CEX

| | Changes in Charge Variants | | | | | |
| --- | --- | --- | --- | --- | --- | --- |
| | T = 0 | | | Week 2 | | |
| AS15802 | 64.9 | 15.5 | 19.6 | 53.5 | 32.7 | 13.8 |
| AS15803 | 61.8 | 17.5 | 20.7 | 51.7 | 37.5 | 10.8 |
| AS15810 | 59.7 | 14 | 26.3 | 49.9 | 36.7 | 13.5 |
| AS15815 | 60.3 | 14.4 | 25.3 | 47 | 40.4 | 12.6 |
| AS15820 | 58.7 | 16.6 | 24.7 | 49.1 | 35.6 | 15.3 |

Example 14. Stability of Humanized Anti-Human IL-17A Monoclonal Antibody Under Low pH Condition for Virus Inactivation 200 μg of the test sample was adjusted to pH 3.4±0.05 with 1 mol/l citric acid mother solution, and the final concentration of the sample was 1 mg/mL. The sample was left at room temperature and sampled at 0, 1, 2, 4 and 6 hours respectively, and the pH was adjusted to 7.5 with 2 mol/l of Tris-HCl pH 9.5 mother solution. The samples were analyzed by the above SEC method, and the result is shown in Table 7. The humanized anti-human IL-17A antibody could tolerant low pH condition for virus inactivation for at least 6 hours, indicating a good stability.

TABLE 7

Stability of Humanized Anti-human IL-17A Monoclonal Antibody under Low pH Condition detected by SE-HPLC

| Humanized Anti-human IL-17A Monoclonal Antibody | SE-HPLC Purity | | | | |
| --- | --- | --- | --- | --- | --- |
| | T = 0 | $1^{st}$ Hour | $2^{nd}$ Hour | $4^{th}$ Hour | $6^{th}$ Hour |
| AS15802 | 99.9% | 99.8 | 99.9 | 99.9 | 99.8 |
| AS15803 | 99.9% | 99.8 | 99.8 | 99.9 | 99.9 |
| AS15810 | 98.0% | 98.1 | 98.1 | 98.0 | 98.2 |
| AS15815 | 98.1% | 98.4 | 98.3 | 98.3 | 98.5 |
| AS15820 | 96.5% | 96.4 | 96.4 | 96.5 | 96.7 |

Example 15 Pharmacokinetics Study of Humanized Anti-Human IL-17A Monoclonal Antibody in Rats Female SD rats, 6 to 8 weeks old, purchased from Beijing Huafukang Biotechnology Co., Ltd., were used as experimental animals. One week after the rats were acclimated to the environment, the rats were randomly divided into groups, 3 rats per group. Anti-human IL-17A chimeric monoclonal antibody and control antibody were administered respectively at a dose of 15 nmol/kg by subcutaneous injection, single administration. At 0, 1 hour, 4 hours, 8 hours, 24 hours, 48 hours, 72 hours, 96 hours, 120 hours, 168 hours, 216 hours, 264 hours, 312 hours, 360 hours, 408 hours and 480 hours after administration, the retro-orbital blood sample was collected without anticoagulation, and the blood sample was allowed to stand at room temperature for 30 minutes to 1 hour; after coagulation, the blood sample was centrifuged at 3,000 rpm for 10 minutes, the obtained serum sample was frozen at −80° C. and stored for testing.

The concentrations of anti-human IL-17A chimeric monoclonal antibody and control antibody in the serum were determined by ELISA. Briefly, human recombinant IL-17A protein was coated on a high-absorbing ELISA plate with a carbonate buffer solution with pH 9.6 at 4° C. overnight. The plate was washed with PBST. To prevent non-specific binding, the plate was blocked with PBST containing 5% nonfat milk powder, and then washed with PBST. Then, the serum sample to be tested diluted with PBST containing 10% mixed rat serum and 1% BSA was added and incubated at 25° C. for 1 hour, and the plate was washed with PBST. Horseradish peroxidase-labeled anti-human IgG antibody (Chemicon, Catalog Number AP309P) diluted in PBST containing 5% skimmed milk powder was added, incubated at 25° C. for 1 hour, the then plate was washed with PBST. Finally, color development was carried out using the colorimetric substrate TMB at room temperature for 10 minutes. Color development was terminated by adding 100 μL/well of 1 M $H_2SO_4$. The absorbance at 450 nm was read on a microplate reader.

Figure 10:
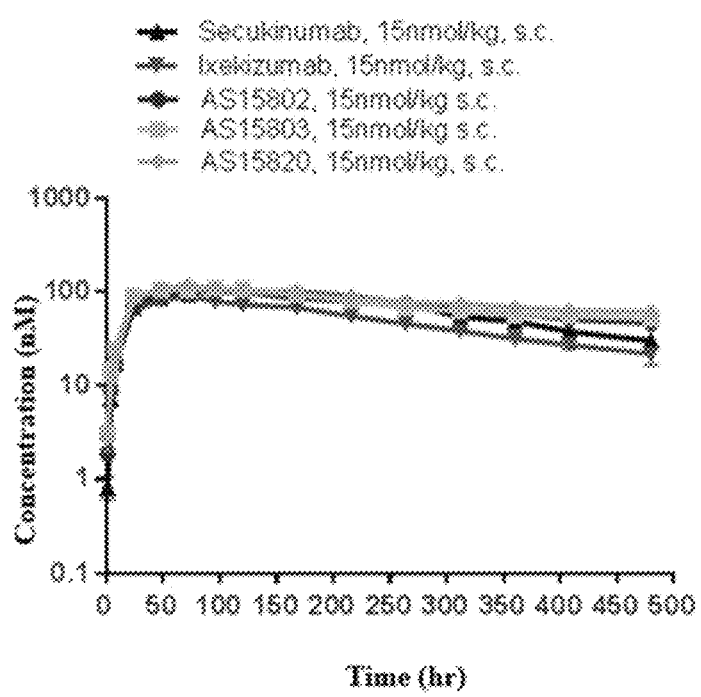
FIG. 10 shows the concentration-time curve after the single subcutaneous injection in Example 15.

The result is shown in FIG. 10. The single subcutaneous injection of 15 nmol/kg of different anti-human IL-17A humanized monoclonal antibody, control monoclonal antibody Secukinumab, and control monoclonal antibody Ixekizumab showed similar concentration-time curves and pharmacokinetic features in vivo.

Finally, it should be understood that the above embodiments are only used to illustrate the technical solution of the present disclosure instead of limiting it; although the present disclosure has been described in detail with reference to the foregoing embodiments, it should be understood by those having ordinary skill in the art that the technical solutions described in the foregoing embodiments may be modified, or some or all of the technical features may be equivalently replaced; and the modifications or replacements, however, would not make the substances of the corresponding technical solutions depart from the scope of the technical solutions of the embodiments of the present disclosure.

Industrial Applicability: the antibody and functional fragment thereof provided by the present disclosure can specifically bind to IL-17A, and can be used for prevention and/or treatment of a disease associated with overexpression and/or over-release of IL-17A, for example, airway inflammation, asthma, bronchial asthma, allergic asthma, chronic obstructive pulmonary disease, idiopathic pulmonary fibrosis, rheumatoid arthritis, osteoarthritis, ankylosing spondylitis, psoriatic arthritis, psoriasis, multiple sclerosis, systemic sclerosis, systemic lupus erythematosus, lupus nephritis, scleroderma, ulcerative colitis, inflammatory bowel disease, uveitis, *Helicobacter pylori*-associated gastritis, osteoporosis, bone erosion, intraperitoneal abscess and adhesions, Addison's disease, gamma globulin deficiency, alopecia areata, celiac disease, Chagas disease, Crohn's disease, allograft rejection, Behcet's disease, sepsis, septic or endotoxin shock and ischemia.

The invention claimed is:

1. An antibody or antigen-binding fragment thereof that specifically binds to IL-17A and comprises a light chain variable region (VL) and a heavy chain variable region (VH); wherein the VL comprises CDR-L1, CDR-L2 and CDR-L3 comprising the amino acid sequences of SEQ ID NO:1, 2 and 3, respectively; and the VH comprises CDR-H1, CDR-H2 and CDR-H3 comprising the amino acid sequences of SEQ ID NO: 4, 5 and 6, respectively.

2. The antibody or antigen-binding fragment thereof according to claim 1, wherein the antibody or antigen-binding fragment thereof comprises a constant region of human IgG1, IgG2, IgG3, IgG4, IgA, IgM, IgE or IgD.

3. The antibody or antigen-binding fragment thereof according to claim 1, wherein the antigen-binding fragment is selected from the group consisting of F(ab')$_2$, Fab', Fab, Fv and scFv.

4. The antibody or antigen-binding fragment thereof according to claim 1, which is a chimeric or humanized antibody or antigen-binding fragment thereof.

5. The antibody or antigen-binding fragment thereof according to claim 4, which is a chimeric antibody or antigen-binding fragment thereof, wherein the VL comprises the amino acid sequence of SEQ ID NO:7, and the VH comprises the amino acid sequence of SEQ ID NO:8.

6. The antibody or antigen-binding fragment thereof according to claim 5, wherein the light chain constant region comprises the amino acid sequence of SEQ ID NO: 9, and the heavy chain constant region comprises the amino acid sequence of SEQ ID NO: 10.

7. The antibody or antigen-binding fragment thereof according to claim 4, which is a humanized antibody or antigen-binding fragment thereof, and comprises the light chain framework regions of FR-L1, FR-L2, FR-L3 and FR-L4, and the heavy chain framework regions of FR-H1, FR-H2, FR-H3 and FR-H4; wherein the FR-L1 comprises the amino acid sequence of SEQ ID NO: 11, or a substitution variant thereof wherein the $1^{st}$ amino acid D is replaced by I, and/or the $2^{nd}$ amino acid V is replaced by I;

the FR-L2 comprises the amino acid sequence of SEQ ID NO: 12, or a substitution variant thereof wherein the $4^{th}$ amino acid F is replaced by Y, and/or the $14^{th}$ amino acid R is replaced by L;

the FR-L3 comprises the amino acid sequence of SEQ ID NO: 13, or a substitution variant thereof wherein the $35^{th}$ amino acid Y is replaced by F;

the FR-L4 comprises the amino acid sequence of SEQ ID NO: 14;

the FR-H1 comprises the amino acid sequence of SEQ ID NO: 15, or a substitution variant thereof wherein the $4^{th}$ amino acid L is replaced by V;

the FR-H2 comprises the amino acid sequence of SEQ ID NO: 16, or a substitution variant thereof wherein the $15^{th}$ amino acid I is replaced by M;

the FR-H3 comprises the amino acid sequence of SEQ ID NO: 17, or a substitution variant thereof wherein the $2^{nd}$ amino acid V is replaced by I; and/or the $6^{th}$ amino acid V is replaced by R; and the FR-H4 comprises the amino acid sequence of SEQ ID NO: 18.

8. The antibody or antigen-binding fragment thereof according to claim 7, wherein the VL comprises an amino acid sequence selected from SEQ ID NO: 19-26.

9. The antibody or antigen-binding fragment thereof according to claim 7, wherein the VH comprises an amino acid sequence selected from SEQ ID NO: 27-34.

10. The antibody or antigen-binding fragment thereof according to claim 7, wherein a) the VL comprises the amino acid sequence of SEQ ID NO: 19; and the VH comprises the amino acid sequence of SEQ ID NO: 27;

b) the VL comprises the amino acid sequence of SEQ ID NO: 20; and the VH comprises the amino acid sequence of SEQ ID NO: 28;

c) the VL comprises the amino acid sequence of SEQ ID NO: 21; and the VH comprises the amino acid sequence of SEQ ID NO: 29;

d) the VL comprises the amino acid sequence of SEQ ID NO: 22; and the VH comprises the amino acid sequence of SEQ ID NO: 30;

e) the VL comprises the amino acid sequence of SEQ ID NO: 22; and the VH comprises the amino acid sequence of SEQ ID NO: 31;

f) the VL comprises the amino acid sequence of SEQ ID NO: 23; and the VH comprises the amino acid sequence of SEQ ID NO: 32;

g) the VL comprises the amino acid sequence of SEQ ID NO: 24; and the VH comprises the amino acid sequence of SEQ ID NO: 33;

h) the VL comprises the amino acid sequence of SEQ ID NO: 25; and the VH comprises the amino acid sequence of SEQ ID NO: 32; or i) the VL comprises the amino acid sequence of SEQ ID NO: 26; and the VH comprises the amino acid sequence of SEQ ID NO: 34.

11. A composition, comprising the antibody or the antigen-binding fragment thereof according to claim 1 and a pharmaceutically acceptable carrier.

12. The composition according to claim 11, wherein the antibody or the antigen-binding fragment thereof is coupled to at least one diagnostic agent and/or therapeutic agent to form an immunoconjugate.

13. The composition according to claim 12, wherein the diagnostic agent is selected from the group consisting of a radionuclide, a radioactive contrast agent, a paramagnetic ion, a metal, a fluorescent label, a chemiluminescent label, an ultrasound contrast agent, and a photosensitizer.

14. The composition according to claim 12, wherein the therapeutic agent is selected from the group consisting of a naked antibody, a cytotoxic agent, a drug, a radionuclide, a boron atom, an immunomodulator, an anti-apoptotic agent, a photosensitizing therapeutic, an immunoconjugate and an oligonucleotide.

15. An isolated nucleic acid molecule selected from:
A) a DNA or RNA encoding the antibody or antigen-binding fragment thereof according to claim 1; and
B) a nucleic acid complementary to the nucleic acid as defined in A).

16. A method of treating a disease associated with IL 17A, comprising administering the antibody or the antigen-binding fragment thereof according to claim 1 to a subject in need thereof.

17. The method according to claim 16, wherein the disease is selected from the group consisting of airway inflammation, asthma, bronchial asthma, allergic asthma, chronic obstructive pulmonary disease, idiopathic pulmonary fibrosis, rheumatoid arthritis, osteoarthritis, ankylosing spondylitis, psoriatic arthritis, psoriasis, multiple sclerosis, systemic sclerosis, systemic lupus erythematosus, lupus nephritis, scleroderma, ulcerative colitis, inflammatory bowel disease, uveitis, *Helicobacter pylori*-associated gastritis, osteoporosis, bone erosion, intraperitoneal abscess and adhesions, Addisons disease, gamma globulin deficiency, alopecia areata, celiac disease, Chagas disease, Crohn's disease, allograft rejection, Behcet's disease, sepsis, septic or endotoxin shock and ischemia.

* * * * *